United States Patent [19]

Kato et al.

[11] Patent Number: 5,426,210

[45] Date of Patent: Jun. 20, 1995

[54] ADDUCT OF CINNAMIC ACID AND GLYCERIN, ULTRAVIOLET ABSORBENT AND EXTERNAL PREPARATION FOR SKIN

[75] Inventors: Mikiko Kato; Reiji Miyahara; Keiichi Uehara; Sadaki Takata, all of Yokohama, Japan

[73] Assignee: Shiseido Co., Ltd., Tokyo, Japan

[21] Appl. No.: 982,757

[22] PCT Filed: May 8, 1992

[86] PCT No.: PCT/JP92/00587

§ 371 Date: Mar. 5, 1993

§ 102(e) Date: Mar. 5, 1993

[87] PCT Pub. No.: WO92/19592

PCT Pub. Date: Nov. 12, 1992

[30] Foreign Application Priority Data

May 9, 1991 [JP] Japan .................... 3-133488

[51] Int. Cl.$^6$ ............ C07C 69/76; A61K 7/44
[52] U.S. Cl. ..................... 560/55; 424/60; 562/465
[58] Field of Search ............ 560/55; 424/60; 562/465

[56] References Cited

PUBLICATIONS

Chemical Abstracts, vol. 106, No. 15, Abstract No. 105(15); 119004c, 1984; F. Clouet, et al. "J. Chromatogrphy".
Tetrahedron Letters, Oct. 1970, vol. 49, W. Oppolzer, et al.; "Intramolekulare Cycloadditionen von N-Alkyl-C-Phenoxymethyl-Nitronen an Ortho-Staendige C=C-Doppelbindungen"; pp. 4313-4314.
France, 6380M; Laboratories Anphar, Nov. 1967.
Chemical & Pharmaceutical Bulletin, vol. 39, No. 9, Sep. 1991; Y. Sashida, et al.; "Studies on the Chemical Constituents of the Bulbs of Lilium Machliniae"; pp. 2362-2368.
Chemical Abstracts, vol. 107, No. 12, Abstract No. 107(12); Sep. 1987; Obata Yasuo; "Fragrance J.," 15(3).
Chemical Abstracts, vol. 99, No. 6, Abstract No. 99(6); 43309u, 1983; R. Roelandts, et al., "Int. J. Dermatology".

Primary Examiner—Paul J. Killos
Attorney, Agent, or Firm—Townsend & Banta

[57] ABSTRACT

An adduct of cinnamic acid and glycerin represented by the following general structural formula (1);

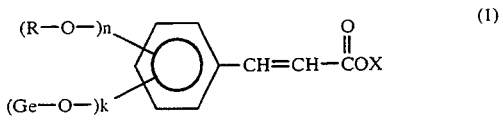

(In the general structural formula (1) above, G represents 1 mole of glycerin and e represents average mole number of addition and at least 1. R represents hydrogen or fatty chain. n and k are identified by that (n+k) is 1 to 3, and n and k are 0 to 3 respectively. X represents hydrogen, ion, fatty chain or Gm, and the G represents 1 mole of glycerin, m represents average number of addition and at least 1.), an ultraviolet ray absorbent and an external preparation for skin containing the same.

The adduct of cinnamic acid and glycerin according to the present invention have excellent capability to absorb ultraviolet rays as well as high water solubility.

4 Claims, 14 Drawing Sheets

ADDUCT OF CINNAMIC ACID AND GLYCERIN, ULTRAVIOLET ABSORBENT AND EXTERNAL PREPARATION FOR SKIN

[TECHNICAL FIELD]

This invention relates to an adduct of cinnamic acid and glycerin, an ultraviolet absorbent and an external preparation for skin and more particularly, a cinnamic acid derivative having ultraviolet absorbancy, and an ultraviolet absorbent and an external preparation for skin using the same.

[BACKGROUND ART]

Various influences of ultraviolet rays to skin, such as rapid aging of the skin, are recently well known. The ultraviolet rays included in sunlight are classified into a long wavelength ultraviolet ray having a wavelength from 400 nm to 320 nm as UV-A, a medium wavelength ultraviolet ray having a wavelength from 320 nm to 290 nm as UV-B, and a short wavelength ultraviolet ray having a wavelength of not more than 290 nm as UV-C in a field of skin science.

Since most of the ultraviolet rays usually irradiated human body originate in sunlight, the UV-C are absorbed by the ozonosphere and the body is mainly influenced by the UV-A and UV-B.

Among these, the UV-B forms erythema or blister and causes aggravation of melanin formation and chromatosis when the skin is irradiated with the UV-B over a certain level.

In order to prevent aging of human skin and generation or increase of blots and flecks thereon, it is very important to protect human skin from the UV-B, and various types of UV-B absorbent have been developed.

The prior UV-B absorbents used for practical application include a PABA derivative, a cinnamic acid derivative, a salicylic acid derivative, a benzophenone derivative, an urocanine derivative, a camphor derivative, and a heterocyclic derivatives.

These types of UV-B absorbents are generally mixed in external preparations for skin such as cosmetics or quasi drugs.

The prior types of UV-B absorbents, however, are oil soluble in most cases and their solubility in water is very low, so their applications have been limited to a narrow area. As a water soluble UV-B absorbent, only 2-hydroxy-4-methoxy-5-sulfoxonium benzophenone sodium salt has been known, however this had not enough ultraviolet ray absorptivity.

[DISCLOSURE OF THE INVENTION]

Accordingly, it is an object of the present invention to eliminate the above-described problems in the prior art and to provide a water soluble material having a high ultraviolet ray absorptivity.

As a result of studies undertaken by the inventors so as to attain this aim, and it has been found that a new adduct of cinnamic acid and glycerin had an excellent ultraviolet ray absorptivity as well as a solubility in water. The present invention has been achieved on the bases of this finding.

The adduct of cinnamic acid and glycerin according to this invention is represented by the following general structural formula (1),

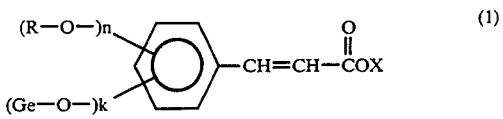

(In the general structural formula (1) above, G represents 1 mole of glycerin, and e represents average mole number of addition and at least 1. R represents hydrogen or fatty chain. n and k are identified by (n+k) is 1 to 3, and n and k are 0 to 3 respectively. X represents hydrogen, ion, fatty chain or Gm, and the G represents 1 mole of glycerin, and m represents average number of addition and at least 1.)

The ultraviolet absorbent according to claim 2 is characterized in that the ultraviolet absorbent is the adduct of cinnamic acid and glycerin represented by the general structural formula (1).

The external preparation for skin according to claim 3 is characterized in that at least one of the adducts of cinnamic acid and glycerin represented by the general structural formula (1) are contained.

Detail structures of this invention will be explained hereinafter.

In the general structural formula (1), R represents a hydrogen or fatty chain. In the case of fatty chain, total number of carbon atoms is preferably 1 to 4. The fatty chain may be any of a straight chain alkyl group, a branched chain alkyl group, an unsaturated alkyl group and a cycloalkyl group. As an example of the R, a methyl group, an ethyl group, an acetylenyl group, a propyl group, an isopropyl group, a propenyl group, a butyl group, an isobutyl group, a t-butyl group, and a butenyl group will be cited. Wavelength of absorbed ultraviolet rays does not differ remarkably in any case, but a methyl group and an ethyl group are especially preferable because of their industrial applicability.

G represents a glyceryl group which correspond to 1 mole of glycerin, but binding type may not be limited. e represents a mole number of the addition. If the number of the e becomes higher, the water solubility becomes higher, but the ultraviolet absorptivity per weight becomes lower. From this reason, the e is preferably in a range from 1 to 10.

X represents a hydrogen, an ion such as a sodium, a potassium, an ammonium, a lower alkyl amine, a triethanol amine, fatty chain having 1 or more carbon atoms and preferably 1 to 4, or Gm. In the case of the X is fatty chain, the fatty chain may be any of a straight chain alkyl group, a branch chain alkyl group, an unsaturated alkyl group and a cycloalkyl group. As an example of the fatty chain, a methyl group, an ethyl group, an acetylenyl group, a propyl group, an isopropyl group, a propenyl group, a butyl group, an isobutyl group, a t-butyl group, and a butenyl group will be cited. Wavelength of absorbed ultraviolet rays does not differ remarkably in any case, but the methyl group and ethyl group are especially preferable because of their solubility in water and industrial applicability. In the case of X is Gm, the G represents a glyceryl group which correspond to 1 mole of glycerin, but binding type may not be limited. m represents an average mole number of the addition and not less than 1 and preferably 1 to 10.

The adduct of cinnamic acid and glycerin described above is in solid or syrupy like state and are extremely excellent in their safety and stability, the adducts can be mixed in chemical products such as dye or ink, plastics, coating agent, chemical fiber, and in addition they can be mixed in pharmaceutical products, quasi drug products, cosmetics and cleaning agents as a component. Furthermore, the adduct has moisture holding ability.

The adduct of cinnamic acid and glycerin according to the present invention can be produced by general method of glycerin addition reactions using an acidic catalyst or alkaline catalyst. Further, transesterification between polyglycerin and cinnamate can be applied.

For example, following method can be applied.

The adduct can be synthesized by dissolving or suspending a compound which is represented by the following general structural formula (2) (in the formula, R, n and K correspond to these of said formula (1)) in a non-aqueous solvent such as dimethylsulfoxide, dimethylformamide, dioxane, dimethylacetamide, N-methylpyrrolidone, N-acetylmorpholine, N-methyl succinimide; by dissolving or suspending the compound represented by the general structural formula (2) in acetone-/aqueous solvent; or without solvent, and mixing the compound with glycidol in the presence of a catalyst under the temperature from 90° to 130° C. This reaction may be carried out under a flow of such a gas as $N_2$ or argon. Further, one or more compounds represented by the general formula (2) may be used in this reaction.

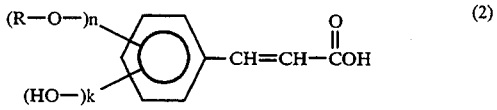

(2)

As an example of the catalyst available in this reaction, a Lewis acidic catalyst such as $BF_3.Et_2O$ and aluminum trichloride; acidic catalyst such as p-toluene sulfonic acid, hereto polyphosphoric acid, phosphoric acid, hydrochloric acid, and sulfuric acid; and alkaline catalyst such as sodium hydroxide, potassium hydroxide, potassium carbonate, sodium carbonate, sodium hydride, sodium alcoholate and sodium will be cited.

Following method can also be applied.

The adduct can be synthesized by dissolving or suspending a compound which can be represented by the following general structural formula (3) (in the formula, R, n and K correspond to these of said formula (1), $R_1$ is lower fatty chain having 1 or more carbon preferably 1 to 4) in a non-aqueous solvent such as dimethylsulfoxide, dimethylformamide, dioxane, dimethylacetamide, N-methylpyrrolidone, N-acetylmorpholine, N-methyl succinimide, and mixing the compound with polyglycerin in the presence of a catalyst under the temperature from 90° to 130° C. This reaction may be carried out under flow of such a gas as $N_2$ or argon, or under reduced pressure condition. Further one or more compounds represented by the general formula (3) may be used in this reaction.

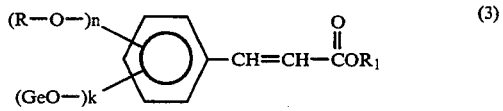

(3)

As an example of catalyst available in this reaction, acidic catalyst such as p-toluene sulfonic acid, hereto polyphosphoric acid, phosphoric acid, hydrochloric acid, and sulfuric acid; alkaline catalyst such as sodium hydroxide, potassium hydroxide, potassium carbonate, sodium carbonate, sodium hydride, sodium alcoholate and sodium; and salt such as ammonium chloride, sodium chloride will be cited.

Further, following method can be applied.

The adduct can be synthesized by dissolving or suspending a compound which can be represented by the following general structural formula (4) (in the formula, R, n and m correspond to these of said formula (2), R represents a lower fatty chain having 1 or more carbon preferably 1 to 4) in a non-aqueous solvent such as dimethylsulfoxide, dimethylformamide, dioxane, dimethylacetamide, N-methylpyrrolidone, N-acetylmorpholine, N-methyl succinimide, and mixing the compound with glycidol in the presence of a catalyst under the temperature from 90° to 130° C. This reaction may be carried out under flow of such a gas as $N_2$ gas or argon. Further, one or more compounds represented by the general formula (4) may be used in this reaction.

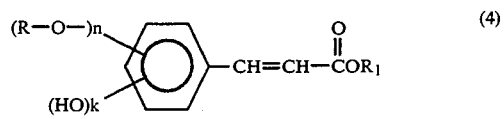

(4)

As an example of the catalyst available in this reaction, a Lewis acidic catalyst such as $BF_3.Et_2O$ and aluminum trichloride; acidic catalyst such as p-toluene sulfonic acid, hetero polyphosphoric acid, phosphoric acid, hydrochloric acid, and sulfuric acid; and alkaline catalyst such as sodium hydroxide, potassium hydroxide, potassium carbonate, sodium carbonate, sodium hydride, sodium alcoholate and sodium will be cited.

After the reaction as described above, the reactant solvent, glycerin and polymerized product of glycerin may be removed by distillation under reduced pressue, or the product may be used as it is.

In the resultant product obtained as described above, however, in addition to the adduct of cinnamic acid and glycerin represented by the general structural formula (1), salt, glycerin, polymerization product of glycerin are contained. In order to remove the glycerin, polymerized product or salt, the product may be purified by extracting with a solvent such as methyl alcohol, ethyl alcohol, butyl alcohol, or isopropyl alcohol; or by distributing it in a mixture of water and methylethyl ketone or n-butanol having a large volume of salt therein and fractionating the organic solvent layer. Also in order to remove glycerin or polymerized product thereof for isolateng the compound, the resultant product may be purified by column chromatography method by suspending the resultant product in water or a mixture of water and alcohol, applying it in a opposite phase partition column such as hyper porous polymer (such as HIPOROUS RESIN supplied from MITSUBISHI KASEI KOGYO KABUSHIKI KAISHA) or octadecyl silica, and then through water as a first eluent and a mixed solution of water with polar organic solvent such alcohol as methanol, ethanol, or acetonitrile as a second eluent, and fractionating and taking out this eluent. Also the resultant product can be purified by recrystallization method.

The adduct of cinnamic acid and glycerin thus obtained are excellent in their resistance to oxidation and chemical stability. As the adduct has glycerin group, the adduct has low stimulus for skin or eye. So the adduct of cinnamic acid and glycerin can be mixed in chemical product such as paint, ink, plastics, coating agents and chemical fiber.

As the adduct of cinnamic acid and glycerin according to the present invention are excellent in their safety, the compound can be mixed in cosmetics or pharmaceutical drugs. In addition to the embodiments of the present invention, the adduct can appropriately be mixed with other components for ordinal cosmetics or pharmaceutical drugs. As an example of such a component, oily components such hydro carbon, fats and oils as liquid paraffin, squalane, vaseline, cetyl alcohol, isostearyl alcohol, cetyl 2-ethylhexanoate, 2-octyldodecyl alcohol, glycerin triisostearate, Macademian nuts oil, and lanolin; wax, silicone, surfactants, thickeners, neutralizers, antiseptics, germicides, anti-oxidants, powder components, pigments, perfumes, other ultraviolet absorbents, drugs, metallic sealant, and pH modifiers will be cited.

The adduct of cinnamic acid and glycerin thus obtained is excellent in their chemical stability and resistance to oxidation, and is also water soluble and can absorb UV-B. Furthermore it is excellent in a moisture holding property.

[BEST MODE FOR CARRYING OUT THE INVENTION]

The embodiments of the present invention will be described hereinafter. It should be noted that the embodiments are not intended to limit the scope of the present invention. A unit for mixing rate is weight %.

EXAMPLE 1

Preparation for the adduct of cinnamic acid and glycerin (1) according to a reaction using acidic catalyst 8.719 g of p-hydroxy cinnamic acid was dissolved in 10 ml of DMSO, and 19.7 g of glycidol was added. The mixture was stirred and heated to 90° C. Catalystic amount of boron trifluoride ethyl ether was added, heating and agitation was carried out for 2 hours and then the adduct of cinnamic acid and glycerin was obtained.

The reaction system was fractionated according to the column chromatography using the hyper porous polymer (HIPOROUS RESIN supplied from MITSUBISHI KASEI KOGYO KABUSHIKI KAISHA), distilled water as a first eluent and a mixture of ethyl alcohol and distilled water with the mixing ratio of 3:7 as second eluent. The fraction of which the mixing ratio of ethyl alcohol and distilled water was 3:7 was evaporated and the adduct of cinnamic acid and glycerin was purified.

The yield of the adduct of cinnamic acid and glycerin was 8.9 g.

0.1 ml of trimethylsilylchlorosilane, 0.1 ml of trimethylsilylimidazole and N,O-bis(trimethylsilyl)acetamide were added to 10 mg of the adduct, heated at 80° C. for 30 minutes and resultant TMS compound was obtained. This TMS compound was applied to a gas chromatography (CHROMATOPACK GC-9A supplied from SHIMAZU CORPORATION, COLUMN; DIASOLID ZT made of glass and having 3$\phi$×50 cm supplied from GASCHRO KOGYO CORPORATION, FLOW RATE; 60 ml/min. N$_2$, DETECTOR; FID, TEMPERATURE UP; 100° C. to 340° C. 10° C./min., TEMPARATURE OF SAMPLE GASIFICATION ROOM; 360° C.) and then analyzed.

Figure 1:
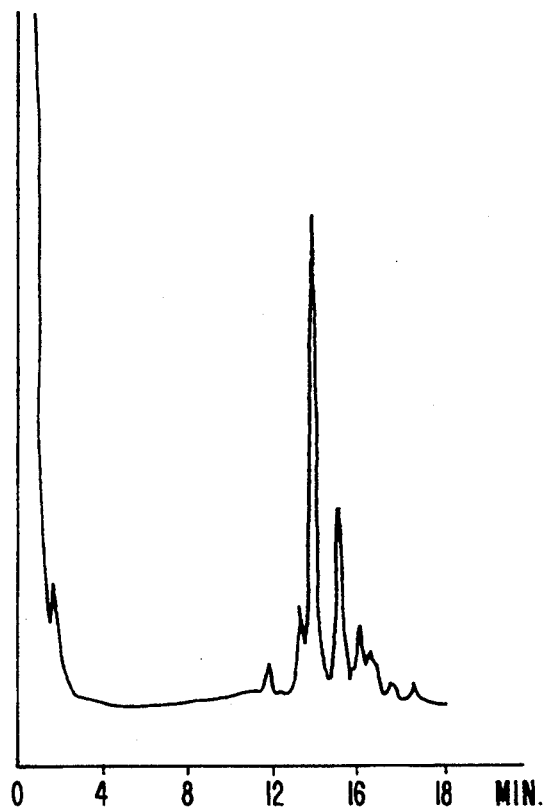
FIG. 1 is a view of a gas chromatogram of an adduct of cinnamic acid and glycerin (mixture) according to the example 1 of the present invention.

The gas chromatogram is shown in FIG. 1.

It will be understood from the FIG. 1 that the adduct of cinnamic acid and glycerin according to the example 1 is a mixture of several compounds. The inventors then conducted separation and identification of the main compounds. As a result of this separation and identification, following compounds (1), (2) were identified.

(1) Adduct of 2 mole glycerin (e=m=1, k=1 and n=0 in the formula 1)

The adduct of 2 mole glycerin represented by the structural formula 5 described below was included in the mixture of adducts manufactured by the example 1.

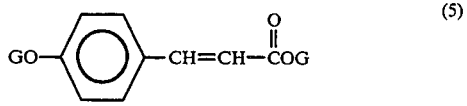
(5)

Namely, the compound which had retention time; 13.9 minutes was isolated and purified by silica gel column chromatography (eluent; chloroform to chloroform/methanol=10:1 (v/v)), and analyzed by methods ① to ⑧. The obtained compound was solid state. This compound was treated as the sample 1.

① GAS CHROMATOGRAPHY 0.1 ml of trimethylsilylchlorosilane, 0.1 ml of trimethylsilylimidazol and N,O-bis(trimethylsilyl)acetamide were added to 10 mg of the adduct, heated at 80° C. for 30 minutes and resultant TMS compound was obtained. This TMS compound was applied to the gas chromatography (CHROMATOPACK GC-9A supplied from SHIMAZU CORPORATION, COLUMN; DIASOLID ZT made of glass and having $3\phi \times 50$ cm supplied from GASCHRO KOGYO CORPORATION, FLOW RATE; 60 ml/min. $N_2$, DETECTOR; FID, TEMPERATURE UP: 100° TO 340° C. 10° C./min., TEMPARATURE OF SAMPLE GASIFICATION ROOM: 360° C.) and then analyzed.

Figure 2:
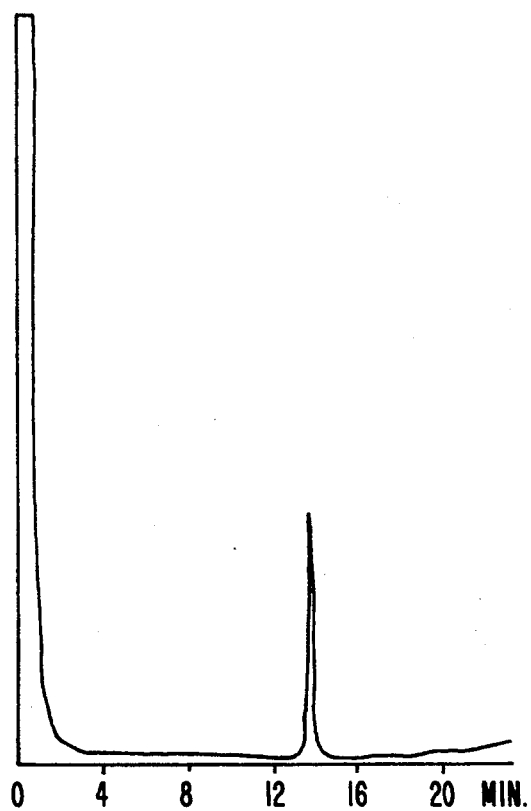
FIG. 2 is a view of a gas chromatogram of glyceryl p-glyceroxy cinnamate (adduct of 2 mole glycerin) according to the example 1 of the present invention.

The gas chromatogram is shown in FIG. 2.

② INFRARED ABSORPTION SPECTROSCOPY

The infrared absorption spectroscopy was measured by using the IRA-1 infrared absorption spectrometer supplied from NIHON BUNKO KABUSHIKI KAISHA with KBr disk, and absorption due to stretching vibration of the hydroxyl group at 3350 $cm^{-1}$, stretching vibration of the glyceroxy group at 2900 $cm^{-1}$ and stretching vibration of the carbonyl group at 1690 $cm^{-1}$ were observed.

Figure 3:
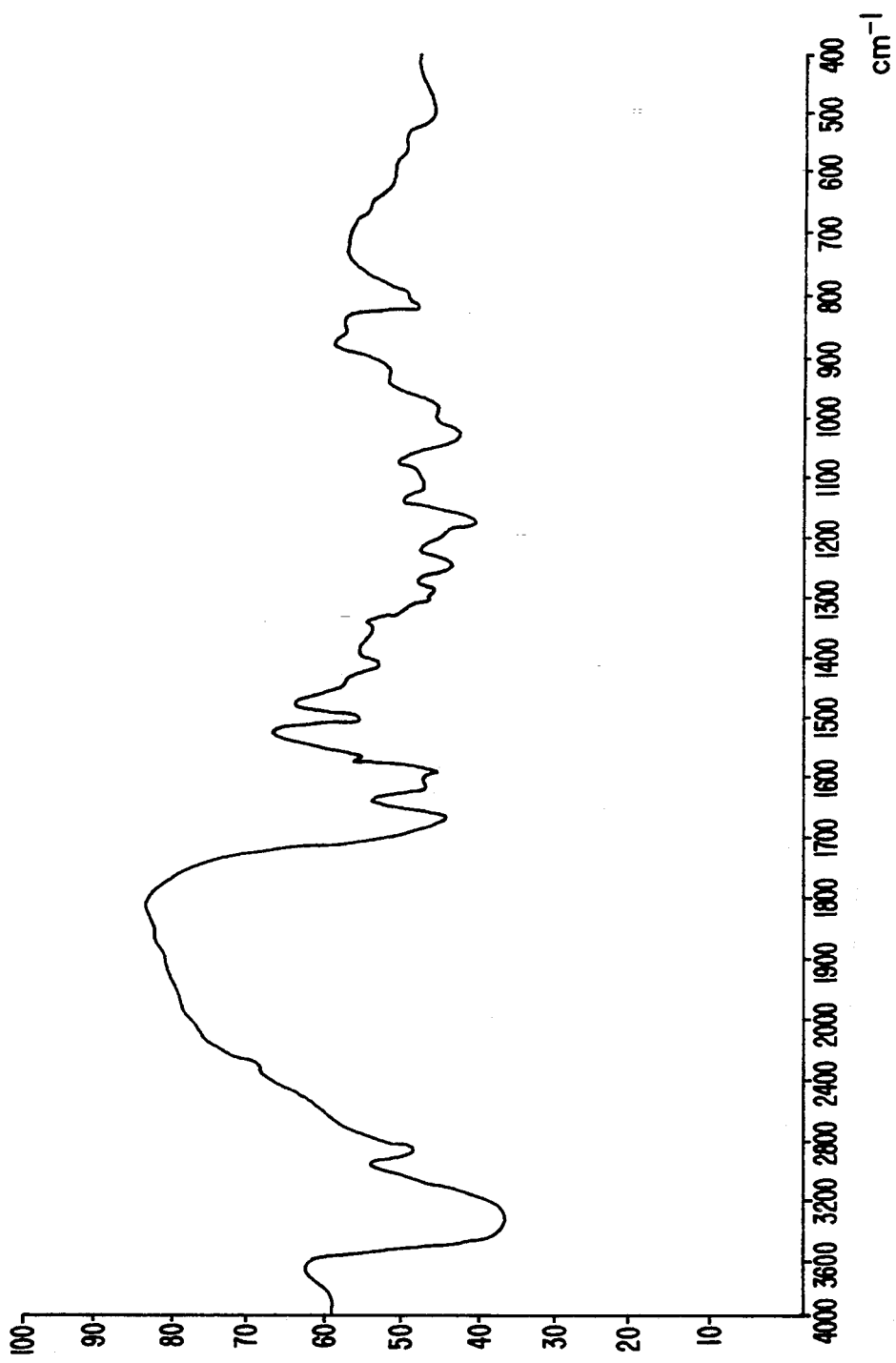
FIG. 3 is a view of an infrared absorption spectrum of glyceryl p-glyceroxy cinnamate (adduct of 2 mole glycerin) according to the example 1 of the present invention.

The result is shown in FIG. 3.

③ $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the cinnamate part were observed at 169 ppm, 162 ppm, 146 ppm, 131 ppm, 128 ppm, and 116 ppm, and signals from carbon atoms in the glyceryl part were observed at 72 ppm, 71 ppm, 70 ppm, 67 ppm and 64 ppm.

Figure 4:
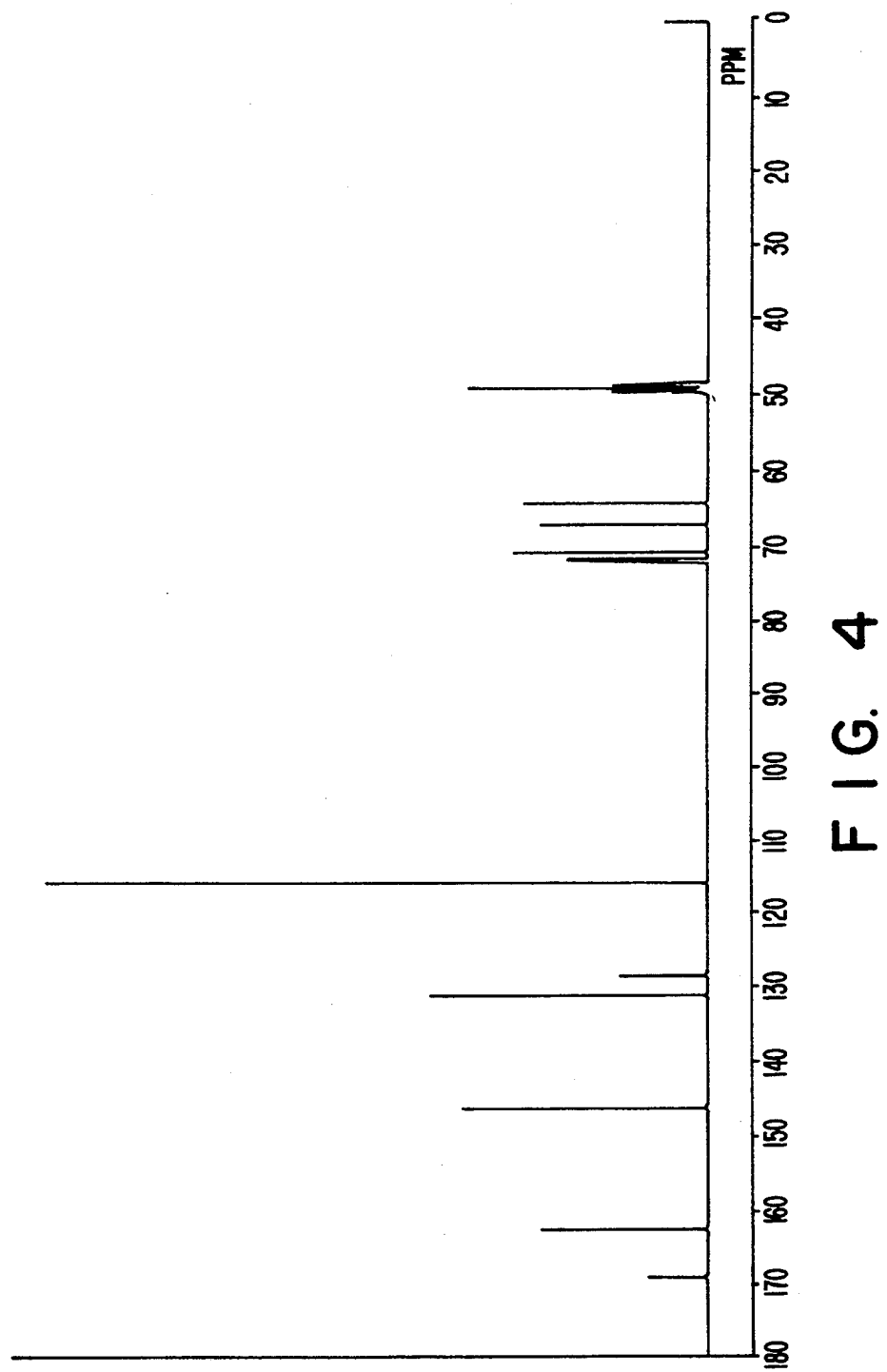
FIG. 4 is a view of a $^{13}$C-NMR spectrum of glyceryl p-glyceroxy cinnamate (adduct of 2 mole glycerin) according to the example 1 of the present invention.

The result is shown in FIG. 4.

④ $^1$H-NMR SPECTROSCOPY

The $^1$H-NMR spectroscopy was measured by using $CD_3OD$ as a solvent with JOEL GX-400 supplied from NIPPON DENSHI KABUSHIKI KAISHA under room temperature. Signals from hydrogen atoms in the cinnamic acid part were observed at $\delta$7.67 (1H, d, J=16 Hz), 7.54 (2H, d, J=8.8 Hz), 7.00 (2H, d, J=8.8 Hz) and 6.40 (1H, d, J=16.1 Hz), and signals from hydrogen atoms in the glyceryl group were observed in a range from $\delta$4.28 to 3.58 ppm.

Figure 5:
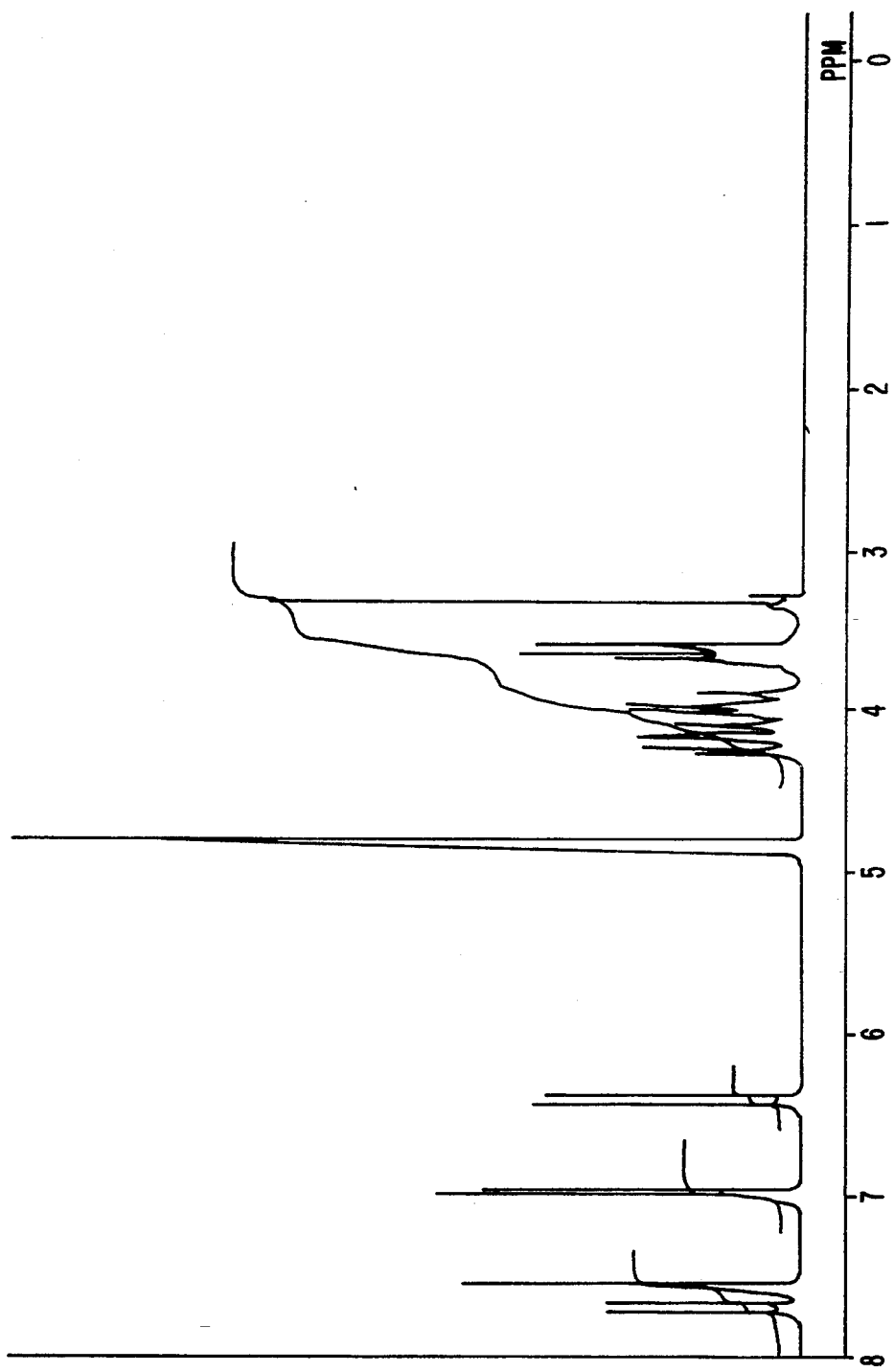
FIG. 5 is a view of a $^1$H-NMR spectrum of glyceryl p-glyceroxy cinnamate (adduct of 2 mole glycerin) according to the example 1 of the present invention.

The result is shown in FIG. 5.

⑤ ULTRAVIOLET RAY ABSORPTION SPECTROSCOPY

The ultraviolet ray absorption spectroscopy was measured by using the UVIDEC 610 C ultraviolet ray absorption spectrometer from NIHON BUNKO KOGYO KABUSHIKI KAISHA with methanol as a solvent. The peak absorptions were observed at 221.4 nm and 309.6 nm.

Figure 6:
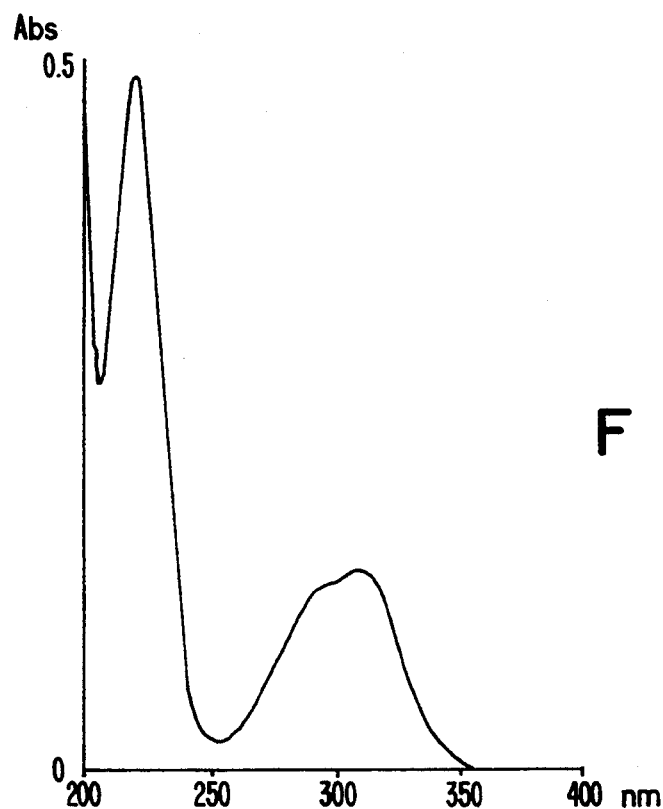
FIG. 6 is a view of an ultraviolet absorption spectrum of glyceryl p-glyceroxy cinnamate (adduct of 2 mole glycerin) according to the example 1 of the present invention.

The result is shown in FIG. 6.

⑥ MELTING POINT

The melting point was measured by using a capillary type melting point measuring apparatus supplied from ARTHUR H. THOMS COMPANY and the melting point was in a range from 116° to 123° C.

⑦ PHENOL INDICATION

The product was spotted on TLC, and phenol indicator was sprayed with a sprayer on it. 10% sodium bicarbonate solution was sprayed over it, but a coloration indicating presence of phenol was not observed.

⑧ BCG INDICATION

The product was spotted on TLC, and BCG indicator was sprayed with a sprayer on it, but a coloration was not observed.

(2) Adduct of 3 mole glycerin (e+m=3, k=1 and n=0 in the general formula 1)

The adduct of 3 mole glycerin represented by the structural formula (6) described below was included in the mixture of adducts manufactured by the example 1.

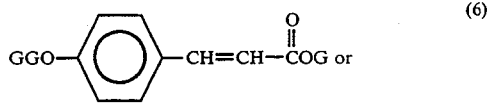
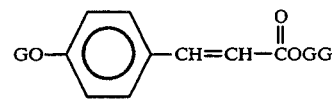
(6)

Namely, the compound which had retention time; 16.3 minutes was isolated and purified by silica gel column chromatography (eluent; chloroform to chloroform/methanol=10:1 (v/v)), and analyzed by methods ① to ④. The obtained compound was solid. This compound was treated as the sample 2.

① GAS CHROMATOGRAPHY 0.1 ml of trimethylsilylchlorosilane, 0.1 ml of trimethylsilylimidazol and N,O-bis(trimethylsilyl)acetamide were added to 10 mg of the adduct, heated at 80° C. for 30 minutes and resultant TMS compound was obtained. This TMS compound was applied to the gas chromatography (CHROMATOPACK GX-9A supplied from SHIMAZU CORPORATION, COLUMN; DIASOLID ZT made of glass and having $3\phi \times 50$ cm supplied from GASCHRO KOGYO CORPORATION, FLOW RATE; 60 ml/min. $N_2$, DETECTOR; FID, TEMPERATURE UP; 100° TO 340° C. 10° C./min., TEMPARATURE OF SAMPLE GASIFICATION ROOM; 360° C.) and then analyzed.

Figure 7:
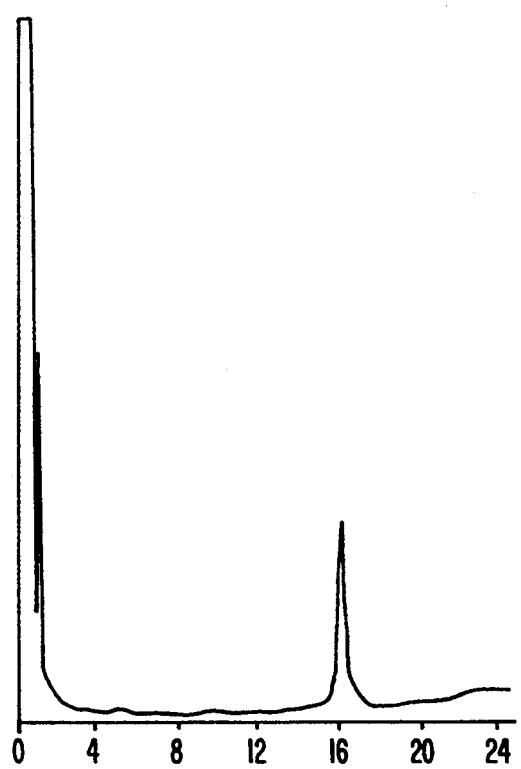
FIG. 7 is a view of a gas chromatogram of glyceryl p-glyceroxy cinnamate (adduct of 3 mole glycerin) according to the example 1 of the present invention.

The gas chromatogram is shown in FIG. 7.

② $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the cinnamate part were observed at 169 ppm, 162 ppm, 146 ppm, 131 ppm, 128 ppm, and 116 ppm, and signals from carbon atoms in the glyceryl group were observed at 72 ppm, 71 ppm, 70 ppm, 67 ppm and 64 ppm.

Figure 8:
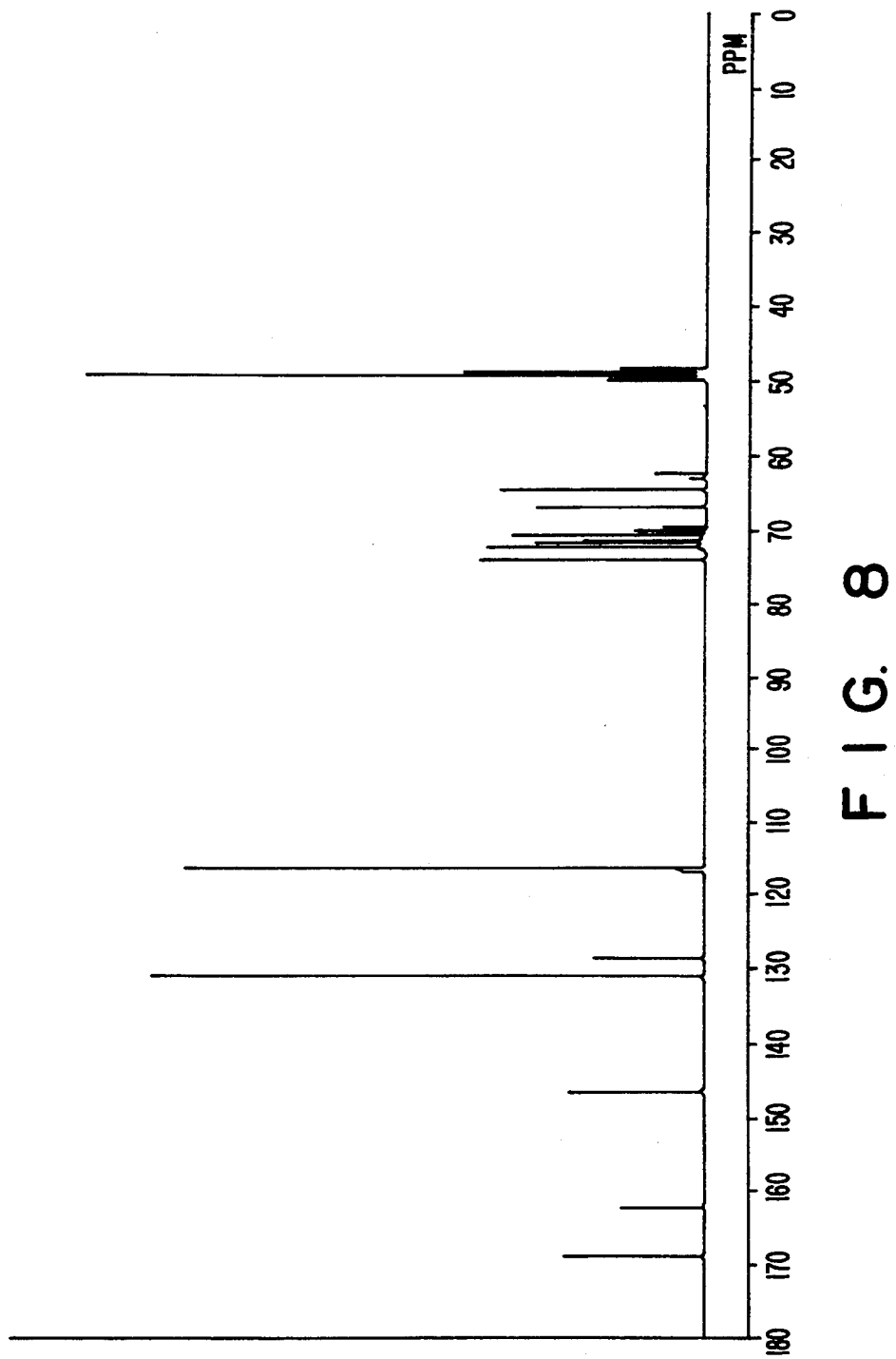
FIG. 8 is a view of a $^{13}$C-NMR spectrum of glyceryl p-glyceroxy cinnamate (adduct of 3 mole glycerin) according to the example 1 of the present invention.

The result is shown in FIG. 8.

③ PHENOL INDICATION

The product was spotted on TLC, and phenol indicator was sprayed with a sprayer on it. 10% sodium bicarbonate solution was sprayed over it, but a coloration indicating presence of phenol was not observed.

④ BCG INDICATION

The product was spotted on TLC, and BCG indicator was sprayed with a sprayer on it, but a coloration was not observed.

EXAMPLE 2

Preparation of the adduct of cinnamic acid and glycerin (2) according to a reaction using acidic catalyst 17.4 g of p-hydroxy cinnamic acid and 40.0 g of glycidol were dissolved in 20 ml of DMSO, and catalytic amount of sulfuric acid was added. The solution was heated to 90° C. and then heating and agitation was carried out for 3 hours, neutralized by adding sodium hydroxide and then adduct of cinnamic acid and glycerin was obtained.

The reaction system was fractionated by column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 18 g.

EXAMPLE 3

Preparation of the adduct of cinnamic acid and glycerin (3) according to a reaction using acidic catalyst 1.74 g of p-hydroxy cinnamic acid and 4.0 g of glycidol were dissolved in 2 ml of DMSO, and catalytic amount of hydrochloric acid was added. The solution was heated to 90° C., heating and agitation were carried out for 1 hour, neutralized by adding sodium hydroxide and then the adduct of cinnamic acid and glycerin was obtained.

The reaction system was fractionated by column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 2 g.

EXAMPLE 4

Preparation of the adduct of cinnamic acid and glycerin (1) according to a reaction using alkaline catalyst 8.719 g of p-hydroxy cinnamic acid was dissolved in 10 ml of DMSO, and 100 mg of sodium hydroxide was added. The mixture was stirred and heated to 90° C. under a flow of $N_2$ gas. 19.7 g of glycidol was added gradually, heating and agitation was carried out for 2 hours, neutralized by adding hydrochloric acid and then the adduct of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The fraction of which the mixing ratio of ethyl alcohol and distilled water was 3:7 was evaporated and the adduct of cinnamic acid and glycerin was purified.

The yield of the adduct of cinnamic acid and glycerin was 13.5 g.

(1) Sodium glyceroxy cinnamate
  (e=3, k=1, n=0 and x=Na)

The adduct of 3 mole glycerin represented by the structural formula (7) described below was included in the mixture of adducts manufactured by the example 4.

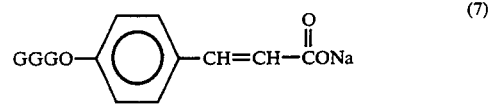

The compound which was synthesized in example 4 was isolated and purified by silica gel column chromatography (eluent; chloroform to chloroform/methanol=10/1 (v/v)), and the obtained solid compound was analyzed by methods ① to ⑤. This compound was treated as sample 3.

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$ and stretching vibration of the carbonyl group at 1690 cm$^{-1}$ were observed.

Figure 9:
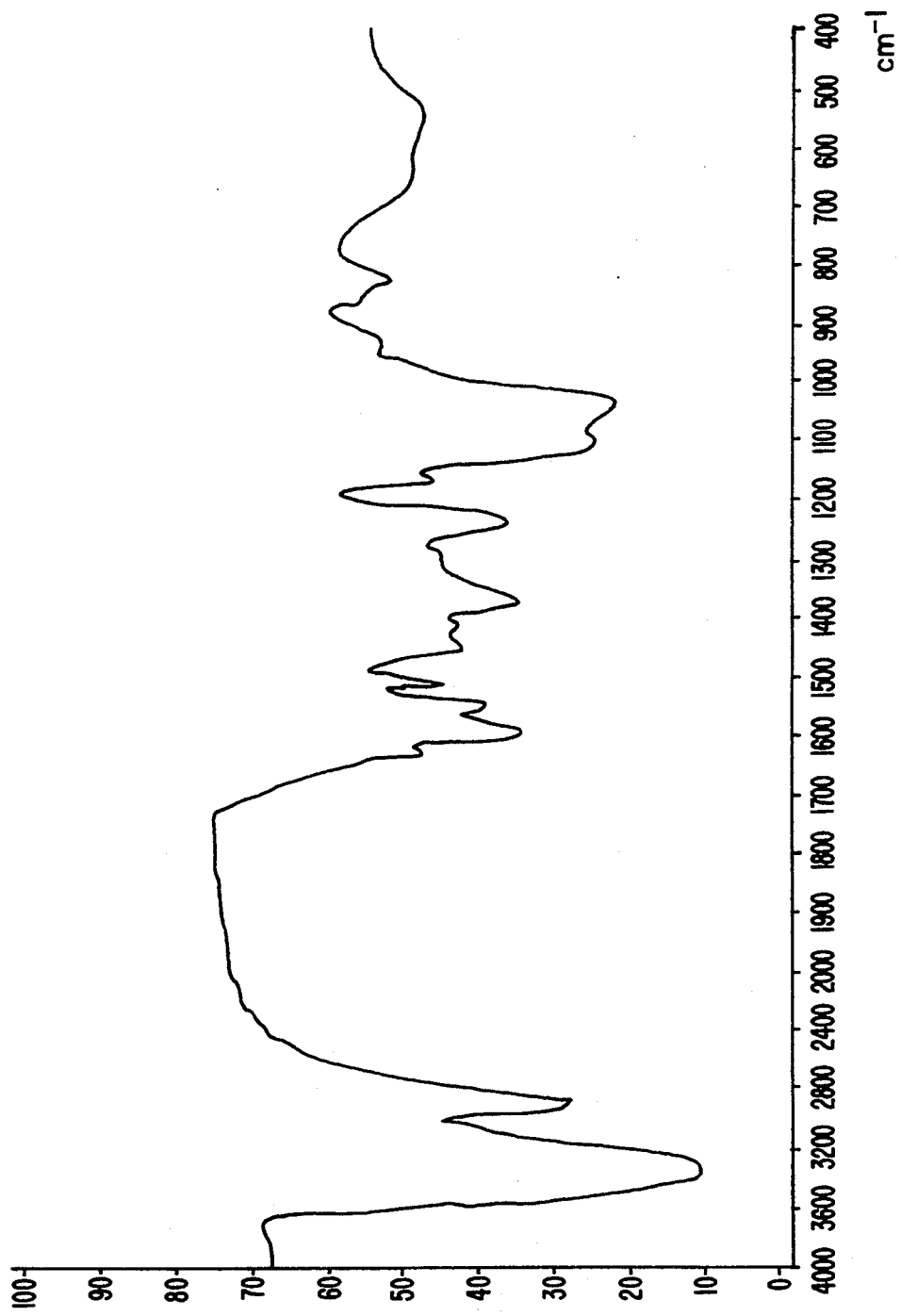
FIG. 9 is a view of an infrared absorption spectrum of glyceryl p-glyceroxy cinnamate (adduct of 3 mole glycerin) according to the example 4 of the present invention.

The result is shown in FIG. 9.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamate ester part were observed at 169 ppm, 162 ppm, 146 ppm, 131 ppm, 128 ppm, 118 ppm and 116 ppm, and signals from carbon atoms in the glyceryl group were observed in a range from 72 ppm to 64 ppm.

Figure 10:
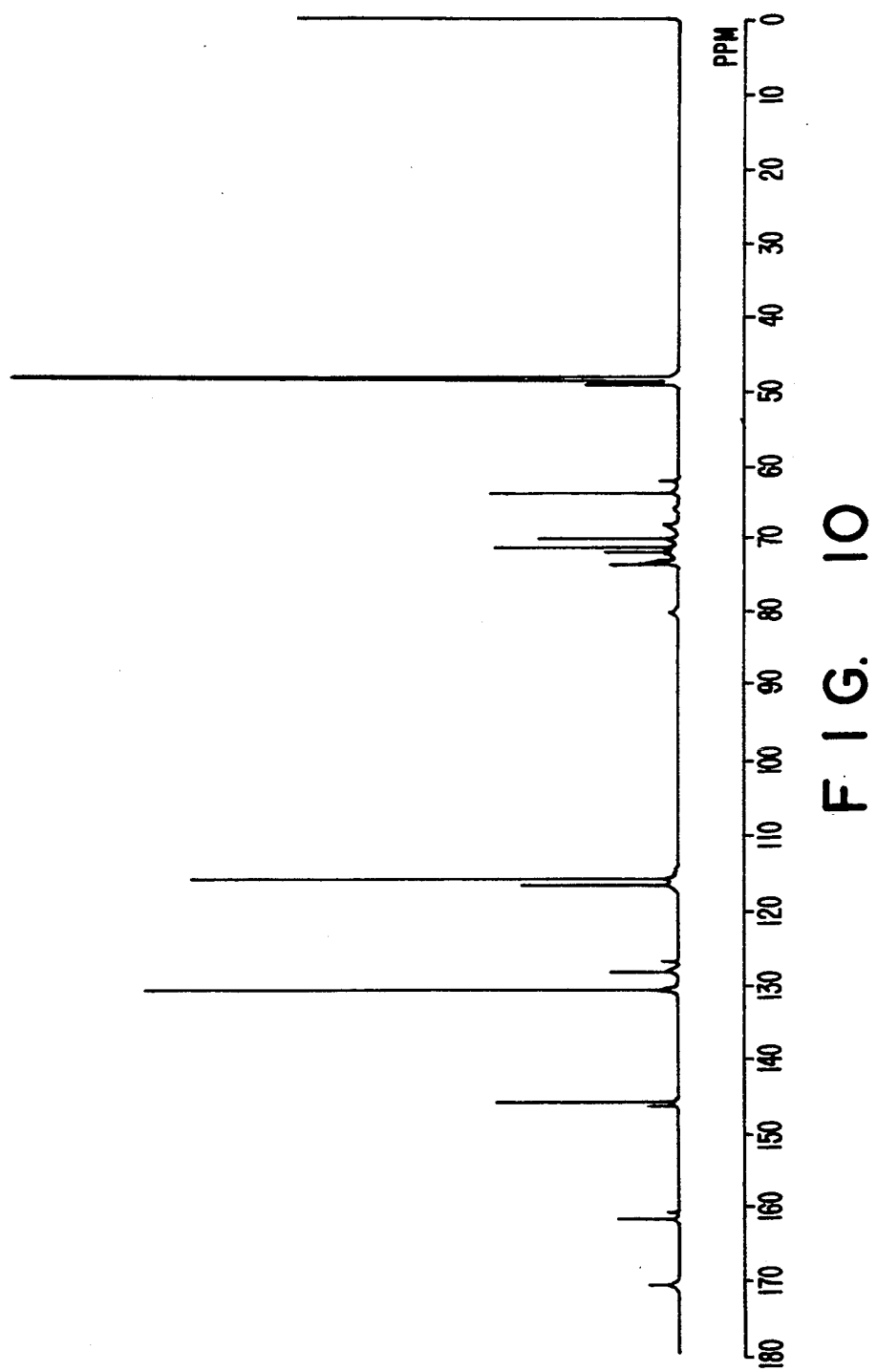
FIG. 10 is a view of a $^{13}$C-NMR spectrum of glyceryl p-glyceroxy cinnamate (adduct of 3 mole glycerin) according to the example 4 of the present invention.

The result is shown in FIG. 10.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA under room temperature. Signals from hydrogen atoms in the cinnamic acid part were observed at δ7.67 (1H, d, J=16 Hz), 7.54 (2H, d, J=8.8 Hz), 7.00 (2H, d, J=8.8 Hz) and 6.40 (1H, d, J=16.1 Hz), and signals from hydrogen atoms in the glyceryl group were observed in a range from δ5.0 to 3.2 ppm.

Figure 11:
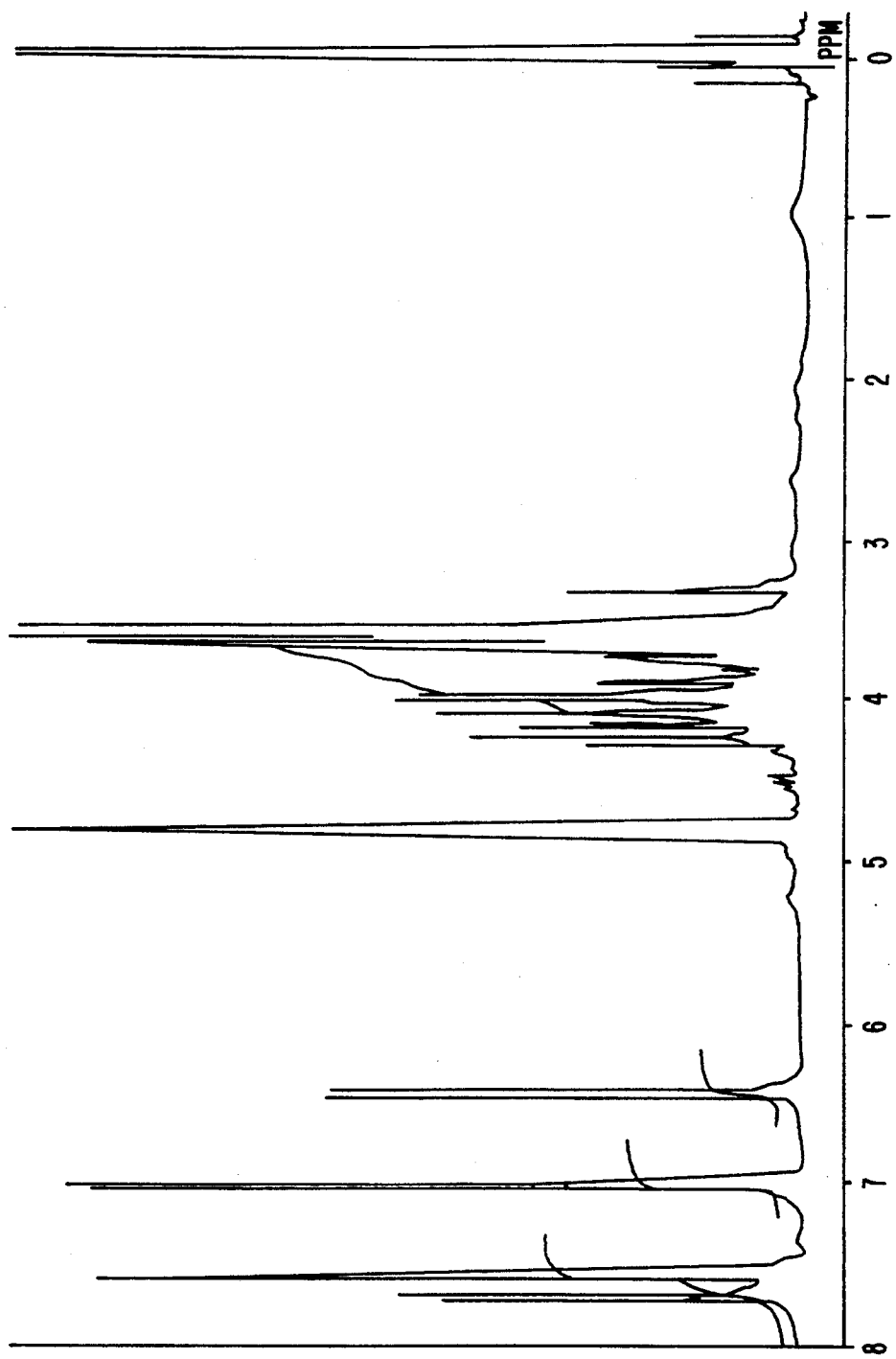
FIG. 11 is a view of a $^1$H-NMR spectrum of glyceryl p-glyceroxy cinnamate (adduct of 3 mole glycerin) according to the example 4 of the present invention.

The result is shown in FIG. 11.

④ ULTRAVIOLET RAY ABSORPTION SPECTROSCOPY

The ultraviolet ray absorption spectroscopy was measured by using the UVIDEC 610 C ultraviolet ray absorption spectrometer from NIHON BUNKO KOGYO KABUSHIKI KAISHA with methanol as a solvent, and the peak absorptions were observed at 222.4 nm and 287.6 nm.

Figure 12:
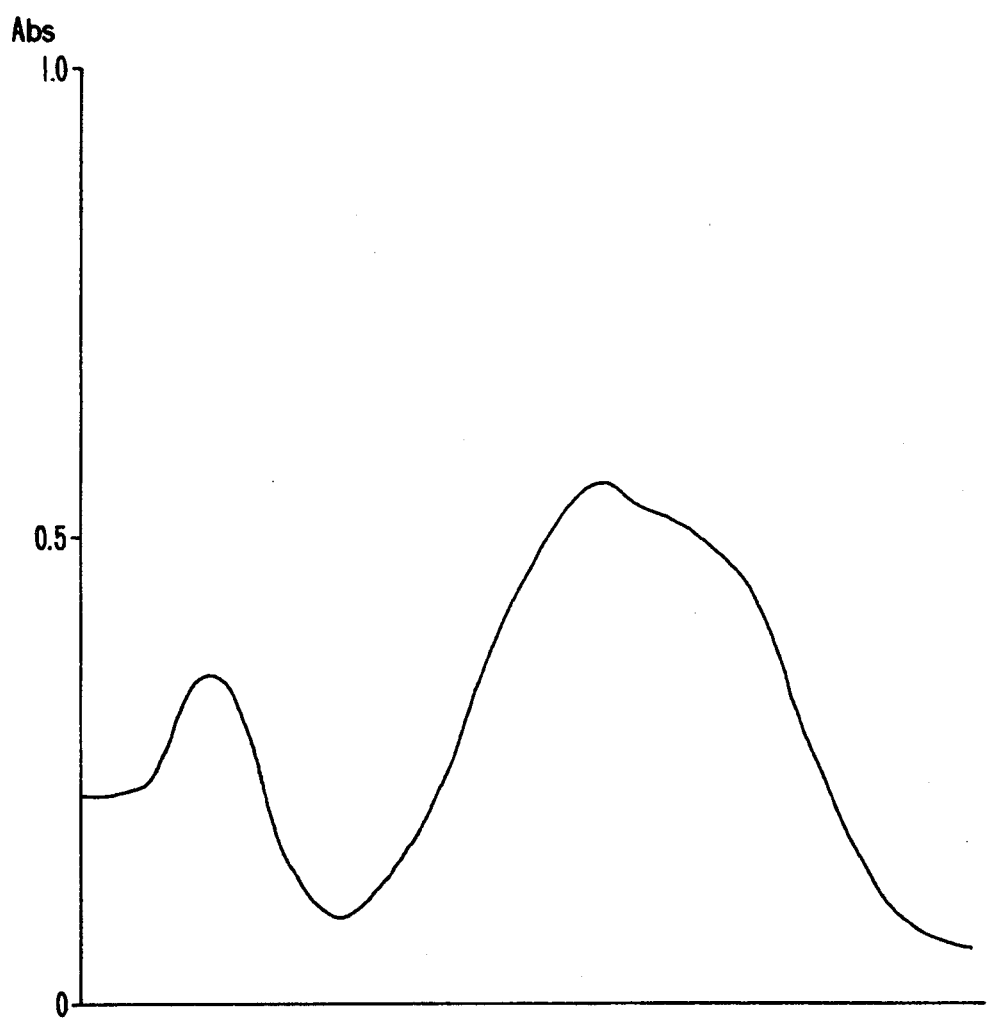
FIG. 12 is a view of an ultraviolet absorption spectrum of glyceryl p-glyceroxy cinnamate (adduct of 3 mole glycerin) according to the example 4 of the present invention.
Figure 13:
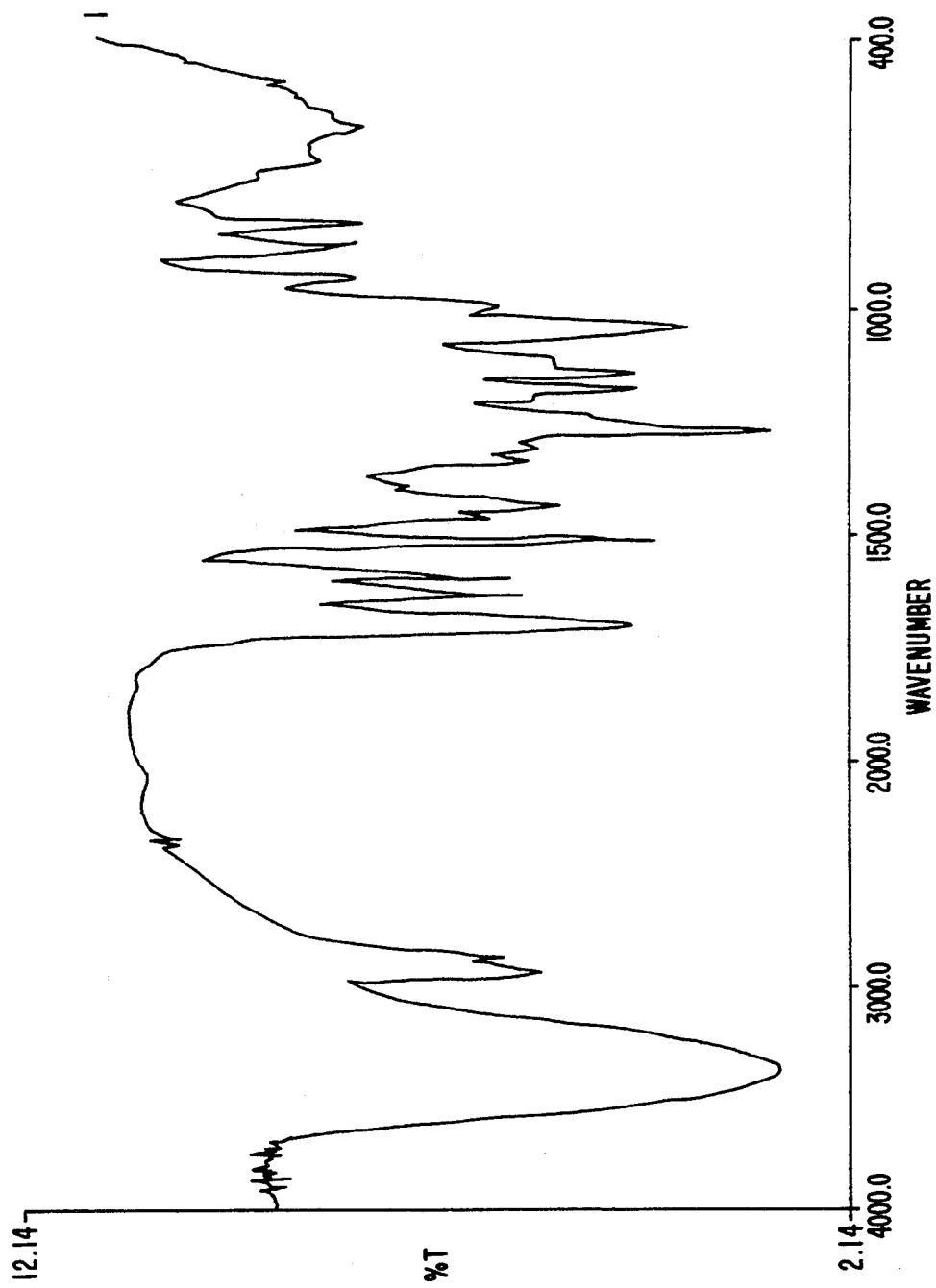
FIG. 13 is a view of an infrared absorption spectrum of glyceroxy cinnamate according to the example 11 of the present invention.

The result is shown in FIG. 12.

⑤ PHENOL INDICATION

The product was spotted on TLC, and a phenol indicator was sprayed with a sprayer on it. 10% sodium bicarbonate solution was sprayed over it, but a coloration indicating presence of phenol was not observed.

EXAMPLE 5

Preparation of the adduct of cinnamic acid and glycerin (2) according to a reaction using alkaline catalyst 4.35 g of p-hydroxy cinnamic acid was dissolved in 5 ml of DMSO, and 50 mg of potassium hydroxide was added. The mixture was stirred and heated to 90° C. under flow of $N_2$ gas. 10.0 g of glycidol was added gradually, heating and agitation was carried out for 1.5 hours, neutralized by adding hydrochloric acid and the adduct of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and adduct of cinnamic acid and glycerin.

The yield of the adduct of cinnamic acid and glycerin was 7.1 g.

EXAMPLE 6

Preparation of the adduct of cinnamic acid and glycerin (3) according to a reaction using alkaline catalyst 2.8 g of p-hydroxy cinnamic acid was dissolved in 3 ml of DMSO, and 10 mg of sodium was added. The mixture was stirred and heated to 90° C. under a flow of $N_2$ gas. 5.0 g of glycidol was added gradually, the heating and agitation was carried out for 1 hours, neutralized by adding hydrochloric acid and then the adduct of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

EXAMPLE 7

Preparation of the adduct of cinnamic acid and glycerin (4) according to a reaction using alkaline catalyst 2.8 g of p-hydroxy cinnamic acid was dissolved in 3 ml of DMSO, and 10 mg of sodium hydride of which the oil was washed by hexane was added. The mixture was stirred and heated to 90° C. under a flow of $N_2$ gas. 5.0 g of glycidol was added gradually, heating and agitation were carried out for 1.5 hours, neutralized by adding hydrochloric acid and then the adduct of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 4.3 g.

EXAMPLE 8

Preparation of the adduct of cinnamic acid and glycerin according to a reaction using transesterification 4.35 g of methyl trimethoxy cinnamate and polyglycerin were dissolved in 5 ml of DMSO. The mixture was stirred and heated to 90° C. under flow of $N_2$ gas and water in the system was removed under reduced pressure condition. 100 mg of potassium carbonate was added, heating and agitation was carried out for 3.5 hours, and then the addition product of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the glyceryl trimethoxy cinnamate represented by the following structural formula (8) was isolated.

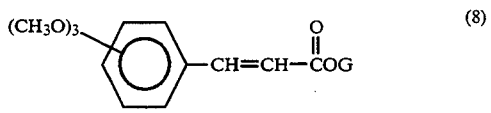

The yield of the glyceryl trimethoxy cinnamate was 5.7 g.

EXAMPLE 9

Preparation of the adduct of cinnamic acid and glycerin (4) according to a reaction using acidic catalyst 4.35 g of trimethoxy cinnamic acid and 10 g of glycidol were dissolved in 5 ml of DMSO. The mixture was stirred and heated to 90° C. Catalystic amount of sulfuric acid was added, heating and agitation were carried out for 3.5 hours, and then the adduct of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and glyceryl trimethoxy cinnamate was isolated.

The yield of the glyceryl trimethoxy cinnamate was 6.1 g.

EXAMPLE 10

Preparation of the adduct of cinnamic acid and glycerin (5) according to a reaction using alkaline catalyst 4.35 g of trimethoxy cinnamic acid and 100 mg of sodium hydroxide were dissolved in 5 ml of DMSO, and the mixture was stirred and heated to 90° C. under a flow of $N_2$ gas. Water in the system was removed under low pressure condition. 10 g of glycidol was added, heating and agitation was carried out for 3 hours, and then the adduct of cinnamic acid and glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the glyceryl trimethoxy cinnamate was obtained.

The yield of the glyceryl trimethyl cinnamate was 5.7 g.

The compound which was synthesized in example 10 was isolated and purified by silica gel column chromatography (eluent; chloroform to chloroform/methanol=10/1 (v/v)), and analyzed by methods ① to ③. The obtained compound was wax like so the melting point of the compound could not be measured. This compound was treated as sample 4.

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$ and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamate part were observed at 169 ppm, 162 ppm, 146 ppm, 131 ppm, 128 ppm, 116 ppm and 115 ppm, signals from carbon atoms in the glyceryl group were observed in a range from 72 ppm to 64 ppm, and signals from carbon atoms in the methyl group was observed at 52 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA under room temperature. Signals from hydrogen atoms in the cinnamic acid part were observed at δ7.67 (1H, d, J=16 Hz), 7.54 (2H, d, J=8.8 Hz), 7.00 (2H, d, J=8.8 Hz) and 6.40 (1H, d, J=16.1 Hz), and signals from hydrogen atoms in the glyceryl group were observed in the range from δ4.28 to 3.58 ppm.

EXAMPLE 11

Methyl Glyceroxy cinnamate 100 mg of p-glyceroxy cinnamic acid was dissolved in 3 ml of methanol. 1 ml of sodium methylate was added and the mixture was stirred under room temperature for 30 minutes. The system was neutralized by adding HCl-MeOH, and then the glyceroxy cinnamate was obtained.

The compound which was evaporated under reduced pressure condition was isolated and purified by silica gel column chromatography using chloroform-methanol as an eluent, and then a solid type glyceroxy cinnamate was obtained.

The yield of the glyceroxy cinnamate was 60 mg.

The compound described above was analyzed by methods ① and ②. This compound was treated as sample 5.

① INFRARED ABSORPTION SPECTROSCOPY

The infrared absorption spectroscopy was measured by using the IRA-1 infrared absorption spectrometer supplied from NIHON BUNKO KABUSHIKI KAISHA with KBr disk, and absorption due to stretching vibration of the hydroxyl group at 3350 cm$^{-1}$, stretching vibration of the glyceroxy group at 2900 cm$^{-1}$ and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamate part were observed at 169 ppm, 162 ppm, 146 ppm, 131 ppm, 128 ppm and 116 ppm, and signals from carbon atoms in the glyceryl group were observed in a range from 72 ppm to 64 ppm.

EXAMPLE 12

Glyceryl m,p-diglyceroxy cinnamate 3.0 g (16.7 mmol) of caffeic acid and 9.9 g (133 mmol) of glycidol were dissolved in 5 ml of DMSO, and the mixture was stirred and heated to 90° C. Catalystic amount of BF$_3$.Et$_2$O was added and, heating and agitation was carried out for 3 hours. The system was cooled by standing in air, and water in the system was removed under reduced pressure condition. The residue was fractionated by the chromatography using the column, DIAION HP20 (MITSUBISHI KASEI KABUSHIKI KAISHA), distilled water as a first eluent and a mixture of EtOH/H$_2$O=3/7 (v/v) as a second eluent. The effluent fraction of which the mixture of EtOH/H$_2$O=3/7 was evaporated and glyceryl m,p-diglyceroxy cinnamate was obtained. The results of analysis of the resultant glyceryl m,p-diglyceroxy cinnamate were indicated below.

① INFRARED ABSORPTION SPECTROSCOPY

The infrared absorption spectroscopy was measured by using the IRA-1 infrared absorption spectrometer supplied from NIHON BUNKO KABUSHIKI KAISHA with KBr disk, and absorption due to stretching vibration of the bond between carbon and oxygen at 3375 cm$^{-1}$, stretching vibration of the bond between carbon and hydrogen at 2940 cm$^{-1}$ and stretching vibration of the carbonyl group at 1700 cm$^{-1}$ were observed.

Figure 14:
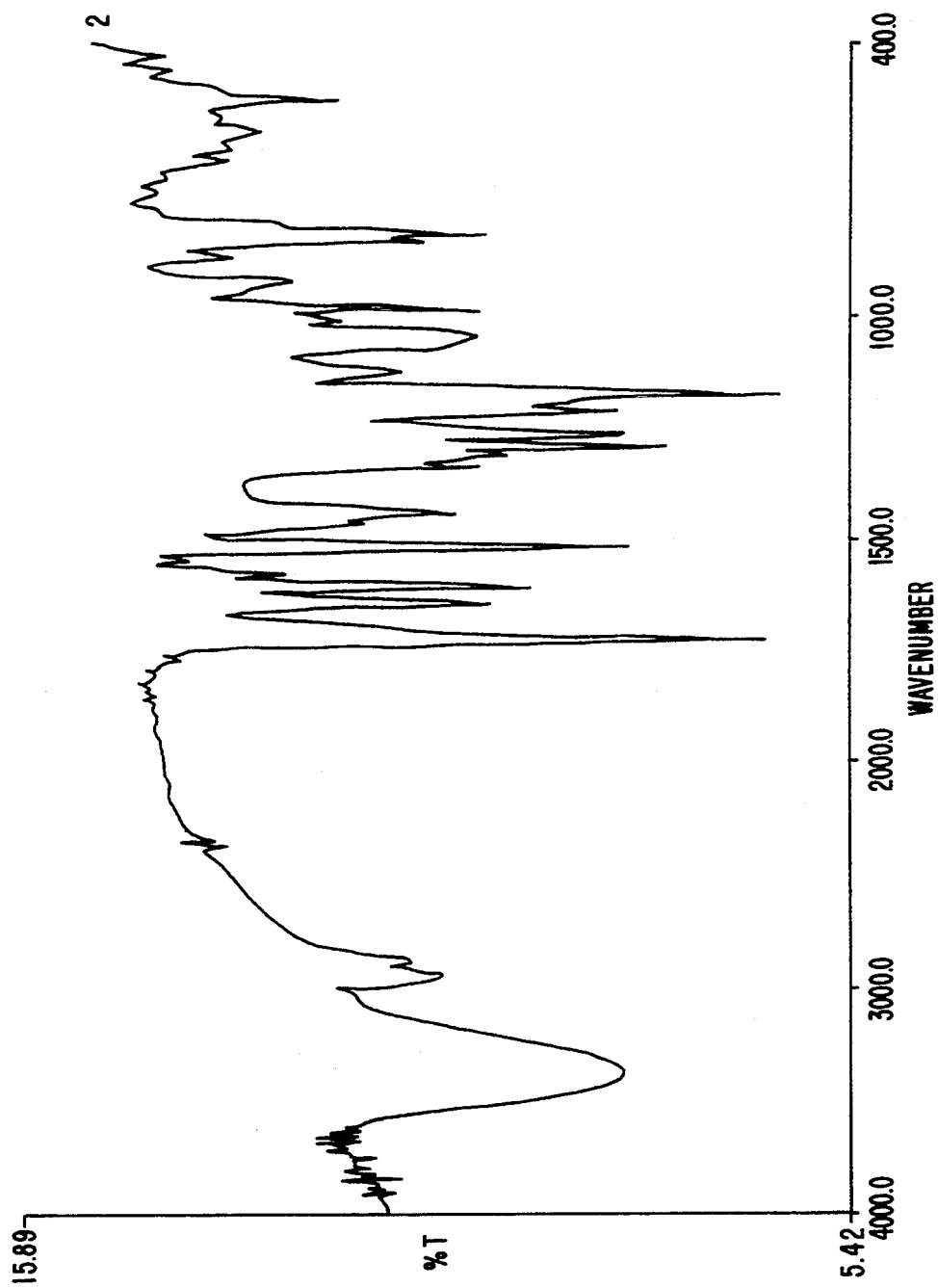
FIG. 14 is a view of an infrared absorption spectrum of glyceryl m,p-glyceroxy cinnamate (adduct of 3 mole glycerin) according to the example 12 of the present invention.

The result is shown in the FIG. 14.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the caffeic acid part were observed in a range from 160 ppm to 103 ppm, and signals from carbon atoms in the glyceryl group were observed in a range from 64 ppm to 43 ppm.

Figure 15:
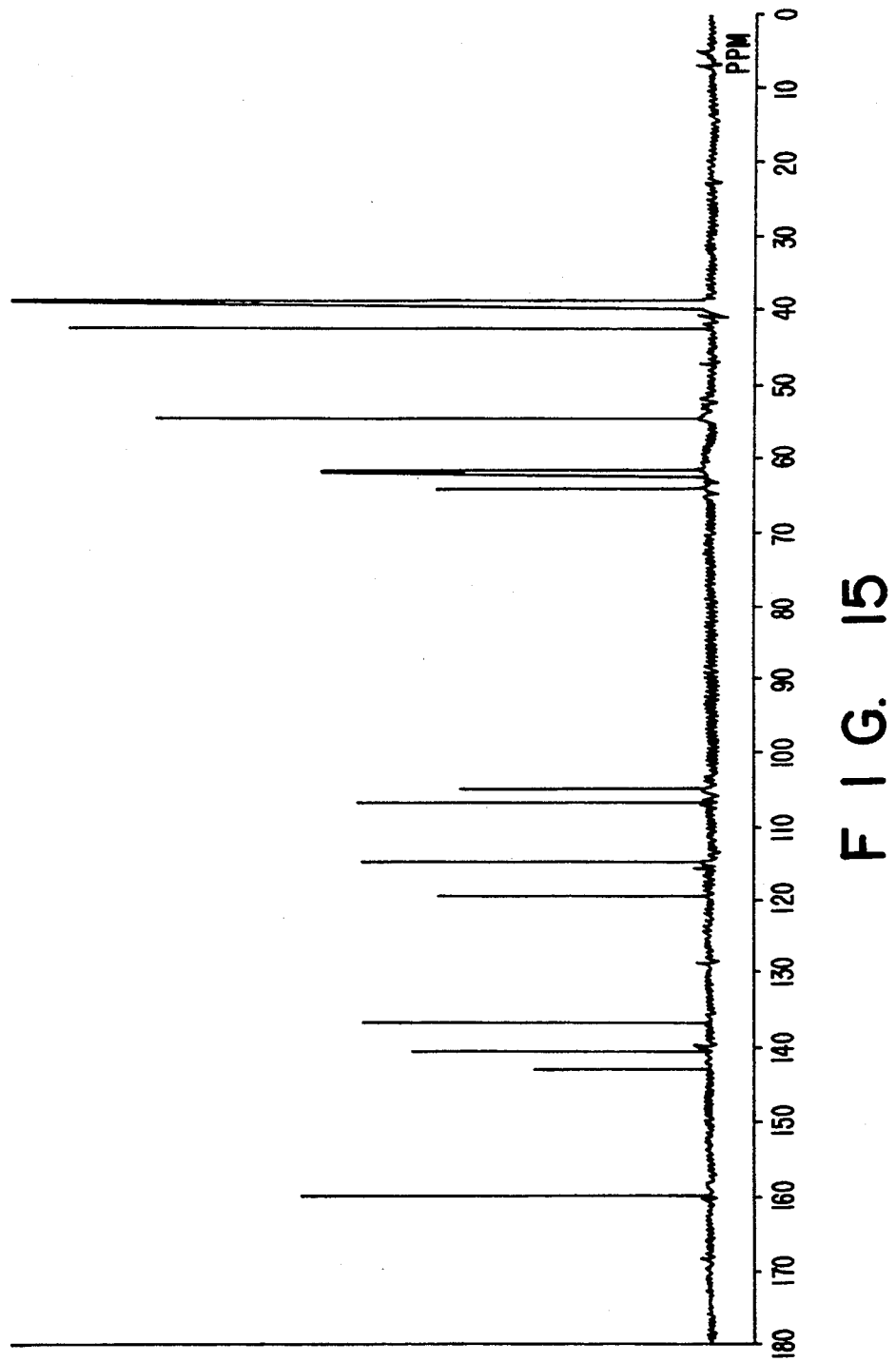
FIG. 15 is a view of a $^{13}$C-NMR spectrum of glyceryl m,p-glyceroxy cinnamate (adduct of 3 mole glycerin) according to the example 12 of the present invention.

The result is shown in the FIG. 15.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA under room temperature. Signals from hydrogen atoms in the caffeic acid part were observed in a range from δ7.62 to 6.374 ppm, and signals from hydrogen atoms in the glyceryl group were observed in a range from δ4.14 to 3.34 ppm.

Figure 16:
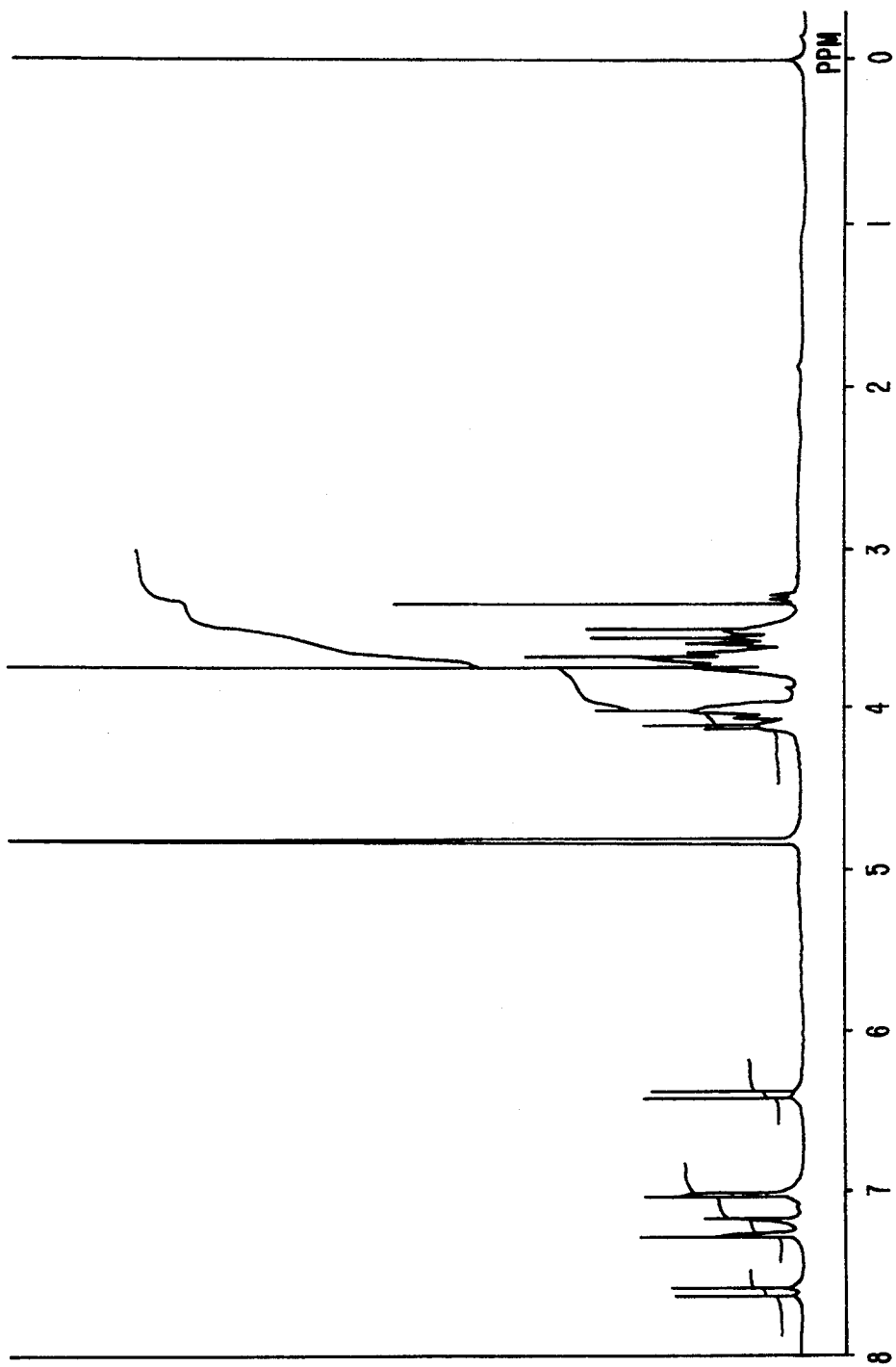
FIG. 16 is a view of a $^1$H-NMR spectrum of glyceryl m,p-glyceroxy cinnamate (adduct of 3 mole glycerin) according to the example 12 of the present invention.

The result is shown in the FIG. 16.

EXAMPLE 13

Glyceryl m-glyceroxy p-methoxy cinnamate (e=1, k=1, m=1, X=G)

3.0 g of ferulic acid was dissolved in 90 ml of DMSO, and 15 g of glycidol was added. Catalystic amount of $BF_3.Et_2O$ was added and the mixture was stirred and heated to 90° C. Heating and agitation was carried out for 2 hours. The system was cooled by standing in air, water in the system was removed and glyceryl m-glyceroxy p-methoxy cinnamate was obtained.

The reaction system was fractionated by the column chromatography using the hyper porous polymer (HIPOROUS RESIN supplied from MITSUBISHI KASEI KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was obtained.

The yield of the adduct of cinnamic acid and glycerin was 3.4 g.

The results of analysis of the obtained glyceryl m-glyceroxy p-methoxy cinnamate was indicated below.

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$ and stretching vibration of the carbonyl group at 1690 $cm^{-1}$ were observed.

② $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 or 3.3 ppm.

EXAMPLE 14

Glyceryl p-glyceroxy m-methoxy cinnamate (e=1, k=1, n=1, X=G)

1 g of isoferulic acid was dissolved in 30 ml of DMSO, and 5 g of glycidol was added. Catalystic amount of $BF_3.Et_2O$ was added and the mixture was stirred and heated to 90° C. Heating and agitation was carried out for 2 hours. The system was cooled, solvent was removed, and then the glyceryl m-glyceroxy p-methoxy cinnamate was obtained.

The reaction system was fractionated by the column chromatography using hyper porous polymer (HIPOROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 1.3 g.

The results of analysis of the obtained glyceryl p-glyceroxy m-methoxy cinnamate are indicated below.

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

② $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

EXAMPLE 15

Preparation of the adduct of cinnamic acid and glycerin (6) according to a reaction using alkaline catalyst 10 g of caffeic acid was dissolved in 90 ml of DMSO, and 100 mg of sodium hydroxide was added. The system was heated to 90° C. and 20 g of glycidol was added. Heating and agitation was carried out for 2 hours. The system was cooled, neutralized by adding hydrochloric acid, solvent was removed and the adduct of glycerin was obtained.

The reaction system was fractionated by the column chromatography ushig hyperporous polymer (HIPOROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was obtained.

The yield of the adduct of cinnamic acid and glycerin was 15.1 g.

It was identified that the adduct of cinnamic acid and glycerin of the example included glycerin m,p-diglyceroxy cinnamate and the following compound (1).

(1) Sodium m,p-diglyceryl cinnamate
(e=1, k=1, n=0, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the caffeic acid part were observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the caffeic acid part were observed in a range from δ7.6 to 6.3 ppm, and signals from hydrogen atoms in the glyceryl group were observed in a range from δ4.1 to 3.3 ppm.

EXAMPLE 16

Preparation of the adduct of cinnamic acid and glycerin (7) according to a reaction using alkaline catalyst 1 g of methyl p-hydroxy cinnamate was dissolved in 10 ml of DMSO, and 112 mg of sodium hydride was added. The system was heated to 90° C. under N$_2$ gas flow and 2.1 g of glycidol was added gradually. Heating and agitation was carried out for 0.5 hours. The system was cooled, neutralized by adding hydrochloric acid, and the adduct of glycerin was obtained.

The reaction system was fractionated by column chromatography using the hyper porous polymer (HIPOROUS RESIN supplied from MITSUBISHI KASEI KABUSHIKI KAISHA), distilled water as a first eluent and a mixture of ethyl alcohol and distilled water with the mixing ratio of 3:7 as a second solvent. The effluent fraction of which the mixing ratio of ethyl alcohol and distilled water was 3:7 was evaporated and the adduct of cinnamic acid and glycerin was purified.

The yield of the adduct of cinnamic acid and glycerin was 1.5 g.

It was identified that the adduct of cinnamic acid and glycerin of the example included following compounds (1) to (10).

(1) Methyl diglyceroxy cinnamate (e=2, k=1, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the caffeic acid part was observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the caffeic acid part were observed in a range from δ7.6 to 6.3 ppm, and signals from hydrogen atoms in the glyceryl group were observed in a range from δ4.1 to 3.3 ppm.

(2) Methyl triglyceroxy cinnamate (e=3, k=1, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

(3) Methyl tetraglyceroxy cinnamate (e=4, k=1, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part was observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in the range from δ4.1 to 3.3 ppm.

(4) Methyl pentaglyceroxy cinnamate
(e=5, k=1, n=0, X=Me)
① INFRARED ABSORPTION SPECTROSCOPY The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part was observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signal from hydrogen atoms in the glyceryl group were observed in the range from δ4.1 to 3.3 ppm.

(5) Glyceryl triglyceroxy cinnamate
(e=3, k=1, n=0, X=G)
① INFRARED ABSORPTION SPECTROSCOPY The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

(6) Glyceryl tetraglyceroxy cinnamate
(e=4, k=1, n=0, X=G)
① INFRARED ABSORPTION SPECTROSCOPY The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part was observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

(7) Glyceryl pentaglyceroxy cinnamate
(e=5, k=1, n=0, X=G)
① INFRARED ABSORPTION SPECTROSCOPY The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signal from hydrogen atoms in the glyceryl group were observed in a range from δ4.1 to 3.3 ppm.

(8) Sodium diglyceroxy cinnamate
(e=2, k=1, n=0, X=Na)
① INFRARED ABSORPTION SPECTROSCOPY The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C.

Signals from the cinnamic acid part were observed in a range from δ7.6 to 6.3 ppm, and signals from hydrogen atoms in the glyceryl group were observed in a range from δ4.1 to 3.3 ppm.

(9) Sodium triglyceroxy cinnamate
(e=3, k=1, n=0, X=Na)

①  INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

②  $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③  $^1$H-NMR SPECTROSCOPY

The $^1$H-NMR spectroscopy was measured by using $CD_3OD$ as a solvent with JOEL GX-400 supplied from NIPPON DENSHI KABUSHIKI KAISHA at 35° C. Signals from the cinnamic acid part were observed in a range from δ7.6 to 6.3 ppm, and signal from hydrogen atoms in the glyceryl group were observed in a range from δ4.1 to 3.3 ppm.

(10) Sodium tetraglyceroxy cinnamate
(e=4, k=1, n=0, X=Na)

①  INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

②  $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group was observed in a range from 64 ppm to 43 ppm.

③  $^1$H-NMR SPECTROSCOPY

The $^1$H-NMR spectroscopy was measured by using $CD_3OD$ as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

The adduct of cinnamic acid and glycerin of the example included methyl glyceroxy cinnamate (e=1, k=1, n=0, X=Me), glyceryl glyceroxy cinnamate (e=1, k=1, n=0, X=G), glyceryl diglyceroxy cinnamate (e=2, K=1, n=0, X=G), and sodium glyceroxy cinnamate (e=1, k=1, n=0, X=Na).

EXAMPLE 17

Preparation of the adduct of cinnamic acid and glycerin (7) according to a reaction using alkaline catalyst 1 g of methyl caffeic acid was dissolved in 10 ml of DMSO, and 240 mg of sodium hydride was added. The system was heated to 90° C. under $N_2$ gas flow and 5 g of glycidol was added gradually. Heating and agitation was carried out for 0.5 hours. The system was cooled, neutralized by adding hydrochloric acid, solvent was removed, and the adduct of glycerin was obtained.

The reaction system was fractionated by the column chromatography using the hyperporous polymer (HI-POROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 1.8 g.

It was identified that the adduct of cinnamic acid and glycerin of the example included following compounds (1) to (9).

(1) Methyl m,p-diglyceroxy cinnamate
(e=2, k=2, n=0, X=Me)

①  INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

②  $^{13}$C-NMR SPECTROSCOPY

The $^{13}$C-NMR spectroscopy was measured by using $CD_3OD$ as a solvent with JOEL GX-400 supplied from NIPPON DENSHI KABUSHIKI KAISHA at 35° C. Signals from carbon atoms in the caffeic acid part were observed in a range from 169 ppm to 103 ppm, and signals from carbon atoms in the glyceryl group were observed in a range from 64 ppm to 43 ppm.

③  $^1$H-NMR SPECTROSCOPY

The $^1$H-NMR spectroscopy was measured by using $CD_3OD$ as a solvent with JOEL GX-400 supplied from NIPPON DENSHI KABUSHIKI KAISHA at 35° C. Signals from the caffeic acid part were observed in a range from δ7.6 to 6.3 ppm, and signal from hydrogen atoms in the glyceryl group were observed in a range from δ4.1 to 3.3 ppm.

(2) Methyl m,p-diglyceroxy cinnamate
(e=3, k=2, n=0, X=Me)

①  INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

②  $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 ppm to 6.3 ppm, and signals from hydrogen atoms in the glyceryl group were observed in a range from δ4.1 to 3.3 ppm.

(3) Methyl m,p-diglyceroxy cinnamate
(e=4, k=2, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the caffeic acid part were observed in a range from δ7.6 ppm to 6.3 ppm, and signals from hydrogen atoms in the glyceryl group were observed in a range from δ4.1 to 3.3 ppm.

(4) Methyl m,p-diglyceroxy cinnamate
(e=2, k=2, n=0, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in the range of δ4.1–3.3 ppm.

(5) Methyl m,p-diglyceroxy cinnamate
(e=3, k=2, n=0, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the caffeic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signal from hydrogen atoms in the glyceryl group were observed in a range from δ4.1 to 3.3 ppm.

(6) Methyl m,p-diglyceroxy cinnamate
(e=4, k=2, n=0, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the caffeic acid part were observed in a range from δ7.6 to 6.3 ppm, and signals from hydrogen atoms in the glyceryl group were observed in a range from δ4.1 to 3.3 ppm.

(7) Sodium m,p-diglyceroxy cinnamate
(e=2, k=2, n=0, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

②  $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part was observed in a range from 169 ppm to 103 ppm, and signals from carbon atoms in the glyceryl group was observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

(8) Sodium m,p-diglyceroxy cinnamate
  (e=3, k=2, n=0, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

(9) Sodium m,p-diglyceroxy cinnamate
  (e=4, k=2, n=0, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the cinnamic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the cinnamic acid part were observed in a range from δ7.6 to 6.3 ppm, and signals from hydrogen atoms in the glyceryl group were observed in a range from δ4.1 to 3.3 ppm.

EXAMPLE 18

Preparation of the adduct of cinnamic acid and glycerin (8) according to a reaction using alkaline catalyst 2 g of methyl ferulate was dissolved in 10 ml of DMSO, and 250 mg of sodium hydride was added. The system was heated to 90° C. under N$_2$ gas flow and 5 g of glycidol was added gradually. Heating and agitation was carried out for 0.5 hours. The system was cooled, neutralized by adding hydrochloric acid, and the adduct of glycerin was obtained.

The reaction system was fractionated by the column chromatography using the hyper porous polymer (HIPOROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 2.3 g.

It was identified that the adduct of cinnamic acid and glycerin of the example included following compounds (1) to (12).

(1) Methyl m-diglyceroxy p-methoxy cinnamate
  (e=2, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(2) Methyl m-triglyceroxy p-methoxy cinnamate
  (e=3, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(3) Methyl m-tetraglyceroxy p-methoxy cinnamate (e=4, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(4) Methyl m-pentaglyceroxy p-methoxy cinnamate (e=5, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(5) Glyceryl m-diglyceroxy p-methoxy cinnamate (e=2, k=1, n=1, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(6) Glyceryl m-triglyceroxy p-methoxy cinnamate (e=3, k=1, n=1, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(7) Glyceryl m-tetraglyceroxy p-methoxy cinnamate (e=4, k=1, n=1, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(8) Glyceryl m-pentaglyceroxy p-methoxy cinnamate
(e=5, k=1, n=1, X=G)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(9) Sodium m-glyceroxy p-methoxy cinnamate
(e=1, k=1, n=1, X=Na)

The adduct of cinnamic acid and glycerin included the above compound.

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(10) Sodium m-diglyceroxy p-methoxy cinnamate
(e=2, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

(11) Sodium m-tetraglyceroxy p-methoxy cinnamate
(e=4, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C.

Signals from the ferulic acid part were observed in a range from δ7.6 to 6.3 ppm, and signals from hydrogen atoms in the glyceryl group were observed in a range from δ4.1 to 3.3 ppm.

(12) Sodium m-pentaglyceroxy p-methoxy cinnamate
(e=5, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range from δ4.1 to 3.3 ppm.

The adduct of cinnamic acid and glycerin of the example included glyceryl m-glyceroxy p-methoxy cinnamate (e=1, k=1, n=1, X=G), and methyl m-glyceroxy p-methoxy cinnamate (e=1, k=1, n=1, X=Me).

EXAMPLE 19

Preparation of the adduct of cinnamic acid and glycerin (9) according to a reaction using alkaline catalyst 3 g of methyl isoferulate was dissolved in 600 ml of DMSO, and 370 mg of sodium hydride was added. The system was heated to 90° C. under N$_2$ gas flow and 7 g of glycidol was added gradually. Heating and agitation was carried out for 0.5 hours. The system was cooled, neutralized by adding hydrochloric acid, solvent was removed and adduct of cinnamic acid and glycerin was obtained.

The reaction system was fractionated by the column chromatography using hyperporous polymer (HIPOROUS RESIN supplied from MITSUBISHI KASEI KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 3.3 g.

It was identified that the adduct of cinnamic acid and glycerin of the example included following compounds (1) to (13).

(1) Methyl p-diglyceroxy m-methoxy cinnamate
(e=2, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(2) Methyl p-triglyceroxy m-methoxy cinnamate
(e=3, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Methyl p-teraglyceroxy m-methoxy cinnamate
(e=4, k=1, n=1, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C.

Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Methyl p-pentaglyceroxy m-methoxy cinnamate
($\underline{e}=5$, $k=1$, $n=1$, $X=Me$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(5) Glyceryl p-diglyceroxy m-methoxy cinnamate
($\underline{e}=2$, $k=1$, $n=1$, $X=G$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(6) Glyceryl p-triglyceroxy m-methoxy cinnamate
($\underline{e}=3$, $k=1$, $n=1$, $X=G$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(7) Glyceryl p-tetraglyceroxy m-methoxy cinnamate
($\underline{e}=4$, $k=1$, $n=1$, $X=G$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(8) Glyceryl p-pentaglyceroxy m-methoxy cinnamate
($\underline{e}=5$, $k=1$, $n=1$, $X=G$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 $cm^{-1}$, stretching vibration of the glyceroxy group at 2900 $cm^{-1}$, and stretching vibration of the carbonyl group at 1690 $cm^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(9) Sodium p-glyceroxy m-methoxy cinnamate
(e=1, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(10) Sodium p-diglyceroxy m-methoxy cinnamate
(e=2, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(11) Sodium p-triglyceroxy m-methoxy cinnamate
(e=3, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(12) Sodium p-tetraglyceroxy m-methoxy sodium cinnamate
(e=4, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using $CD_3OD$ as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using $CD_3OD$ as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(13) Sodium p-pentaglyceroxy m-methoxy cinnamate
(e=5, k=1, n=1, X=Na)

① INFRARED ABSORPTION SPECTROSCOPY

The infrared absorption spectroscopy was measured by using the IRA-1 infrared absorption spectrometer supplied from NIHON BUNKO KABUSHIKI KAI- SHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

②  $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The 1H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

The adduct of cinnamic acid and glycerin of the example included glyceryl p-glyceroxy m-methoxy cinnamate (e=1, k=1, n=1, X=G), and methyl p-glyceroxy m-methoxy cinnamate (e=1, k=1, n=1, X=Me).

EXAMPLE 20

Preparation of the adduct of cinnamic acid and glycerin (10) according to a reaction using alkaline catalyst 1 g of ethyl p-hydroxy cinnamate was dissolved in 10 ml of DMSO, and 125 mg of sodium hydride was added. The system was heated to 90° C. under N$_2$ gas flow and 2.5 g of glycidol was added gradually. Heating and agitation was carried out for 0.5 hours. The system was cooled, neutralized by adding hydrochloric acid, solvent was removed, and adduct of glycerin was obtained.

The reaction system was fractionated by the column chromatography using the hyperporous polymer (HIPOROUS RESIN supplied from MITSUBISHI KASEI KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 2.3 g.

It was identified that the adduct of cinnamic acid and glycerin of the example included following compounds (1) to (5).

(1) Ethyl p-glyceroxy cinnamate
(e=1, k=1, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(2) Ethyl p-diglyceroxy cinnamate
(e=2, k=1, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(3) Ethyl p-triglyceroxy cinnamate
(e=3, k=1, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Ethyl p-tetraglyceroxy cinnamate
(e=4, k=1, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from $\delta$7.6 to 6.3 ppm, and signals from hydrogen atoms in the glyceryl group were observed in a range of $\delta$4.1 to 3.3 ppm.

(5) Ethyl p-pentaglyceroxy cinnamate
(e=5, k=1, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from $\delta$7.6 to 6.3 ppm, and signals from hydrogen atoms in the glyceryl group were observed in a range of $\delta$4.1 to 3.3 ppm.

The adduct of cinnamic acid and glycerin of the example included glyceryl p-glyceroxy cinnamate (e=1, k=1, n=0, X=G), glyceryl p-diglyceroxy cinnamate (e=2, k=1, n=0, X=G), glyceryl p-triglyceroxy cinnamate (e=3, k=1, n=0, X=G), glyceryl p-tetraglyceroxy cinnamate (e=4, k=1, n=0, X=G), glyceryl p-pentaglyceroxy cinnamate (e=5, k=1, n=0, X=G), sodium p-glyceroxy cinnamate (e=1, k=1, n=0, X=Na), Sodium p-diglyceroxy cinnamate (e=2, k=1, n=0, X=Na), sodium p-triglyceroxy cinnamate (e=3, k=1, n=0, X=Na), sodium p-tetraglyceroxy cinnamate (e=4, k=1, n=0, X=Na), and sodium p-pentaglyceroxy cinnamate (e=5, k=1, n=0, X=Na).

EXAMPLE 21

Preparation of the adduct of cinnamic acid and glycerin (11) according to a reaction using alkaline catalyst 5 g of ethyl isoferulate was dissolved in 100 ml of DMSO, and 500 mg of sodium hydride was added. The system was heated to 90° C. under N$_2$ gas flow and 10 g of glycidol was added gradually. Heating and agitation was carried out for 0.5 hours. The system was cooled, neutralized by adding hydrochloric acid, the solvent was removed, and the adduct of glycerin was obtained.

The reaction system was fractionated by the HYPERPOROUS POLYMER (Hi-porous resin supplied from MITSUBISHI KASEI KOGYO KABUSHIKI KAISHA) using distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 6.3 g.

It was identified that the adduct of cinnamic acid and glycerin of the example included following compounds (1) to (5).

(1) Ethyl p-glyceroxy m-methoxy cinnamate
(e=1, k=1, n=1, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from $\delta$7.6 to 6.3 ppm, and signals from hydrogen atoms in the glyceryl group were observed in a range of $\delta$4.1 to 3.3 ppm.

(2) Ethyl p-diglyceroxy m-methoxy cinnamate
(e=2, k=1, n=1, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(3) Ethyl p-triglyceroxy m-methoxy cinnamate
(e=3, k=1, n=1, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Ethyl p-tetraglyceroxy m-methoxy cinnamate
(e=4, k=1, n=1, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(5) Ethyl p-pentaglyceroxy m-methoxy cinnamate
(e=5, k=1, n=1, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② ¹³C-NMR SPECTROSCOPY

The ¹³C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

The adduct of cinnamic acid and glycerin of the example included glyceryl p-glyceroxy m-methoxy cinnamate (e=1, k=1, n=1, X=G), glyceryl p-diglyceroxy m-methoxy cinnamate (e=2, k=1, n=1, X=G), glyceryl p-triglyceroxy m-methoxy cinnamate (e=3, k=1, n=1, X=G), glyceryl p-tetraglyceroxy m-methoxy cinnamate (e=4, k=1, n=1, X=G), glyceryl p-pentaglyceroxy m-methoxy cinnamate (e=5, k=1, n=1, X=G), sodium p-glyceroxy m-methoxy cinnamate (e=1, k=1, n=1, X=Na), sodium p-diglyceroxy m-methoxy cinnamate (e=2, k=1, n=1, X=Na), sodium p-triglyceroxy m-methoxy cinnamate (e=3, k=1, n=1, X=Na), sodium p-tetraglyceroxy m-methoxy cinnamate (e=4, k=1, n=1, X=Na), and sodium p-pentaglyceroxy m-methoxy cinnamate (e=5, k=1, n=1, X=Na).

EXAMPLE 22

Preparation of the adduct of cinnamic acid and glycerin (12) according to a reaction using alkaline catalyst 10 g of ethyl ferulate was dissolved in 100 ml of DMSO, and 1 g of sodium hydride was added. The system was heated to 90° C. under N$_2$ gas flow and 25 g of glycidol was added gradually. Heating and agitation was carried out for 0.5 hours. The system was cooled, neutralized by adding hydrochloric acid, solvent was removed and the adduct of glycerin was obtained.

The reaction system was fractionated by the column chromatography using hyper porous polymer (HIPOROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction in which the mixing ratio of ethyl alcohol and distilled water was 3:7 was evaporated and the adduct of cinnamic acid and glycerin was purified.

The yield of the adduct of cinnamic acid and glycerin was 6.3 g.

It was identified that the adduct of cinnamic acid and glycerin of the example included following compounds (1) to (5).

(1) Ethyl m-glyceroxy p-methoxy cinnamate
($e=1$, $k=1$, $n=1$, $X=Et$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(2) Ethyl m-diglyceroxy p-methoxy cinnamate
($e=2$, $k=1$, $n=1$, $X=Et$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(3) Ethyl m-triglyceroxy p-methoxy cinnamate
($e=3$, $k=1$, $n=1$, $X=Et$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Ethyl m-tetraglyceroxy p-methoxy cinnamate
($e=4$, $k=1$, $n=1$, $X=Et$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(5) Ethyl m-pentaglyceroxy p-methoxy cinnamate
($e=5$, $k=1$, $n=1$, $X=Et$)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C.

Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD₃OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

The adduct of cinnamic acid and glycerin of the example included glyceryl m-glyceroxy p-methoxy cinnamate (e=1, k=1, n=1, X=G), glyceryl m-diglyceroxy p-methoxy cinnamate (e=2, k=1, n=1, X=G), glyceryl m-triglyceroxy p-methoxy cinnamate (e=3, k=1, n=1, X=G), glyceryl m-tetraglyceroxy p-methoxy cinnamate (e=4, k=1, n=1, X=G), glyceryl m-pentaglyceroxy p-methoxy cinnamate (e=5, k=1, n=1, X=G), sodium m-glyceroxy p-methoxy cinnamate (e=1, k=1, n=1, X=Na), sodium m-diglyceroxy p-methoxy cinnamate (e=2, k=1, n=1, X=Na), sodium m-triglyceroxy p-methoxy cinnamate (e=3, k=1, n=1, X=Na), sodium m-tetraglyceroxy p-methoxy cinnamate (e=4, k=1, n=1, X=Na), and sodium m-pentaglyceroxy p-methoxy cinnamate (e=5, k=1, n=1, X=Na).

EXAMPLE 23

Preparation of the adduct of cinnamic acid and glycerin (13) according to a reaction using alkaline catalyst 2 g of ethyl caffeic acid was dissolved in 20 ml of DMSO, and 250 mg of sodium hydride was added. The system was heated to 90° C. under N₂ gas flow and 5 g of glycidol was added gradually. Heating and agitation was carried out for 0.5 hours. The system was cooled, neutralized by adding hydrochloric acid, solvent was removed, and the adduct of glycerin was obtained.

The reaction system was fractionated by the column chromatography using hyper porous polymer (HIPOROUS RESIN supplied from MITSUBISHI KASEI KOGYO KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of cinnamic acid and glycerin was purified.

The yield of the adduct of cinnamic acid and glycerin was 2.3 g.

It was identified that the adduct of cinnamic acid and glycerin of the example included following compounds (1) to (5).

(1) Ethyl m,p-glyceroxy cinnamate (e=1, k=2, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm⁻¹, stretching vibration of the glyceroxy group at 2900 cm⁻¹, and stretching vibration of the carbonyl group at 1690 cm⁻¹ were observed.

② ¹³C-NMR SPECTROSCOPY

The ¹³C-NMR spectroscopy was measured by using CD₃OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD₃OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(2) Ethyl m,p-diglyceroxy cinnamate (e=2, k=2, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm⁻¹, stretching vibration of the glyceroxy group at 2900 cm⁻¹, and stretching vibration of the carbonyl group at 1690 cm⁻¹ were observed.

② ¹³C-NMR SPECTROSCOPY

The ¹³C-NMR spectroscopy was measured by using CD₃OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD₃OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(3) Ethyl m,p-triglyceroxy cinnamate (e=3, k=2, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm⁻¹, stretching vibration of the glyceroxy group at 2900 cm⁻¹, and stretching vibration of the carbonyl group at 1690 cm⁻¹ were observed.

② ¹³C-NMR SPECTROSCOPY

The ¹³C-NMR spectroscopy was measured by using CD₃OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ ¹H-NMR SPECTROSCOPY

The ¹H-NMR spectroscopy was measured by using CD₃OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Ethyl m,p-tetraglyceroxy cinnamate
(e=4, k=2, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(5) Ethyl m,p-pentaglyceroxy cinnamate
(e=5, k=2, n=0, X=Et)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

The adduct of cinnamic acid and glycerin of the example included glyceryl m,p-glyceroxy cinnamate (e=1, k=2, n=0, X=G), glyceryl m,p-diglyceroxy cinnamate (e=2, k=2, n=0, X=G), glyceryl m,p-triglyceroxy cinnamate (e=3, k=2, n=0, X=G), glyceryl m,p-tetraglyceroxy cinnamate (e=4, k=2, n=0, X=G), glyceryl m,p-pentaglyceroxy cinnamate (e=5, k=2, n=0, X=G), sodium m,p-glyceroxy cinnamate (e=1, k=2, n=0, X=Na), sodium m,p-diglyceroxy cinnamate (e=2, k=2, n=0, X=Na), sodium m,p-triglyceroxy cinnamate (e=3, k=2, n=0, X=Na), sodium m,p-tetraglyceroxy cinnamate (e=4, k=2, n=0, X=Na), and sodium m,p-pentaglyceroxy cinnamate (e=5, k=2, n=0, X=Na).

EXAMPLE 24

Preparation of the adduct of cinnamic acid and glycerin (14) according to a reaction using alkaline catalyst 6 g of methyl caffeic acid was dissolved in 60 ml of DMSO, and 750 mg of sodium hydride was added. The system was heated to 90° C. under N$_2$ gas flow and 15 g of glycidol was added gradually. Heating and agitation was carried out for 0.5 hours. The system was cooled, neutralized by adding hydrochloric acid, solvent was removed and the adduct of glycerin was obtained.

The reaction system was fractionated by the column chromatography using hyperporous polymer (HIPOROUS RESIN supplied from MITSUBISHI KASEI KABUSHIKI KAISHA), distilled water as a first eluent and a mixture of ethyl alcohol and distilled water with the mixing ratio of 3:7 as a second eluent. The effluent fraction of which the mixing ratio of ethyl alcohol and distilled water was 3:7 was evaporated and the adduct of glycerin was obtained.

The yield of the adduct of cinnamic acid and glycerin was 2.3 g.

It was identified that the adduct of cinnamic acid and glycerin of the example included following compounds (1) to (5).

(1) Methyl m,p-glyceroxy cinnamate
(e=1, k=2, n=0, X=Mt)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(2) Methyl m,p-diglyceroxy cinnamate
(e=2, k=2, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(3) Methyl m,p-triglyceroxy cinnamate
(e=3, k=2, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(4) Methyl m,p-tetraglyceroxy cinnamate
(e=4, k=2, n=0, X=Me)

② INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

(5) Methyl m,p-pentaglyceroxy cinnamate
(e=5, k=2, n=0, X=Me)

① INFRARED ABSORPTION SPECTROSCOPY

The infrared absorption spectroscopy was measured by using the IRA-1 infrared absorption spectrometer supplied from NIHON BUNKO KABUSHIKI KAISHA with neat, and absorption due to stretching vibration of the hydroxyl group at 3350 cm$^{-1}$, stretching vibration of the glyceroxy group at 2900 cm$^{-1}$, and stretching vibration of the carbonyl group at 1690 cm$^{-1}$ were observed.

② $^{13}$C-NMR SPECTROSCOPY

The $^{13}$C-NMR spectroscopy was measured by using CD$_3$OD as a solvent with JOEL GX-400 supplied from NIPPON DENSHI KABUSHIKI KAISHA at 35° C. Signals from carbon atoms in the ferulic acid part were observed in a range from 169 ppm to 103 ppm, and signals from carbon atoms in the glyceryl group were observed in a range from 64 ppm to 43 ppm.

③ $^1$H-NMR SPECTROSCOPY

The $^1$H-NMR spectroscopy was measured by using CD$_3$OD as a solvent with JOEL GX-400 supplied from NIPPON DENSHI KABUSHIKI KAISHA at 35° C. Signals from the ferulic acid part were observed in a range from δ7.6 to 6.3 ppm, and signals from hydrogen atoms in the glyceryl group were observed in a range of δ4.1 to 3.3 ppm.

The adduct of cinnamic acid and glycerin of the example included glyceryl m,p-glyceroxy cinnamate (e=1, k=2, n=0, X=G), glyceryl m,p-diglyceroxy cinnamate (e=2, k=2, n=0, X=G), glyceryl m,p-triglyceroxy (e=3, k=2, n=0, X=G), glyceryl m,p-tetraglyceroxy cinnamate (e=4, k=2, n=0, X=G), glyceryl m,p-pentaglyceroxy cinnamate (e=5, k=2, n=0, X=G), sodium m,p-glyceroxy cinnamate (e=1, k=2, n=0, X=Na), sodium m,p-diglyceroxy cinnamate (e=2, k=2, n=0, X=Na), sodium m,p-triglyceroxy cinnamate (e=3, k=2, n=0, X=Na), sodium m,p-tetraglyceroxy cinnamate (e=4, k=2, n=0, X=Na), and sodium m,p-pentaglyceroxy cinnamate (e=5, k=2, n=0, X=Na).

Effects of external preparations for skin including above mentioned adduct of cinnamic acid and glycerin will be explained hereinafter.

Experiment 1 Skin Lotion

According to the formulation as shown in table 1, the example 1 represents a skin lotion which was prepared with the adduct of cinnamic acid and glycerin, and the control 1 represents a skin lotion which was prepared with sodium 2-hydroxy-4-methoxybenzophenone-5-sulfonate.

TABLE 1

| COMPONENT | EXAMPLE 1 | CONTROL 1 |
|---|---|---|
| A. (ALCOHOL PHASE) | | |
| Ethanol | 5.0 | 5.0 |
| POE oleyl alcohol ether | 2.0 | 2.0 |
| Perfume | q.s. | q.s. |
| B. (AQUEOUS PHASE) | | |

TABLE 1-continued

| COMPONENT | EXAMPLE 1 | CONTROL 1 |
|---|---|---|
| 1,3-butylene glycol | 5.0 | 5.0 |
| Sample 1 | 8.0 | — |
| Sodium 2-hydroxy-4-methoxy benzophenone-5-sulfonate | — | 8.0 |
| Triethanol amine | 0.1 | 0.1 |
| Carboxy vinyl polymer | 0.15 | 0.15 |
| Distilled water | Residual | Residual |

The alcohol phase A was added to the aqueous phase B, and a perfume was made water soluble to obtain a skin lotion.

In example 1, the skin lotion which has not color and is transparent with viscosity was obtained, while in control 1 a lotion which was yellow color and has no viscosity was obtained.

Experiment 2 Test for Anti-suntan Effect

Field test were carried out on a beach using 2 types of skin lotions prepared in Experiment 1. In the experiment, two samples were respectively applied to right and left halves of each member of a group consisting of 20 men and 20 women, and degree of sun burning was determined. The criterion for the determination was as follows.

| Criterion for evaluation of sun-burning degree | |
|---|---|
| Remarkable erythema recognized | X |
| Slight erythema recognized | Δ |
| Erythema not recognized | O |

The results are shown in Table 2.

TABLE 2

| | APPLIED SECTION of EXAMPLE 1 | APPLIED SECTION of CONTROL 1 | |
|---|---|---|---|
| O | 35 | 6 | |
| Δ | 5 | 12 | |
| X | 0 | 22 | |
| NUMBER OF SKIN TROUBLE CASES | NONE | ITCHINESS ERUPTION | 10 CASES 2 CASES |

From the results as described above, the external preparation for skin containing the adduct of cinnamic acid and glycerin is more effective for protection from ultraviolet rays than that of containing the prior types of water soluble ultraviolet ray absorbent is mixed, and has higher safety without causing any skin trouble.

Experiment 3 Moisture Holding Property

Changes of skin conductance in a group consisting of 15 men and 15 women were measured under the environmental condition of the room temperature of 25° C. and the relative humidity of 50%. The skin lotion produced in Experiment 1 was applied to an arm of each member of the group, and the skin conductance of the arm skin was measured at 24 hours after the treatment. The moisture holding property was determined according to the increase ratio. Results of the determination were as follows.

Increase rate of conductance =

$$\frac{\text{Increase ratio of conductance value}}{\text{Conductance value before treatment}}$$

| Criterion for the capability to preserve humidity | | |
|---|---|---|
| Increase ratio of conductance: | less than 15% | X |
| Increase ratio of conductance: | 15% to 30% | Δ |
| Increase ratio of conductance: | 30% or more | O |

The results are as shown in Table 3.

TABLE 3

| | APPLIED SECTION of EXAMPLE 1 | APPLIED SECTION of CONTROL 1 |
|---|---|---|
| O | 21 | 6 |
| Δ | 9 | 8 |
| X | 0 | 16 |

From the results as described above, it was shown that the external preparation for skin with the adduct of cinnamic acid and glycerin according to the present invention mixed therein is more excellent in its moisture holding property than the external preparation with the prior types of water soluble ultraviolet absorbent.

The examples of external preparation for skin according to the invention will be explained hereinafter. These external preparations for skin had excellent ultraviolet shielding effect.

Example 25 Cream

| A. Oily phase | |
|---|---|
| Stearic acid | 10.0 |
| Stearyl alcohol | 4.0 |
| Monoglycerin stearate | 8.0 |
| Vitamin E acetate | 0.5 |
| Perfume | 0.4 |
| Ethyl paraben | 0.1 |
| Butyl paraben | 0.1 |
| Propyl paraben | 0.1 |
| B. Aqueous phase | |
| Propylene glycol | 8.0 |
| Glycerin | 2.0 |
| Glyceryl p-glyceroxy cinnamate | 6.0 |
| Potassium hydrate | 0.4 |
| Trisodium edetate | 0.05 |
| Distilled water | Residual |

<Preparation process>

The oily phase A and the aqueous phase B are heated to 70° C. and completely dissolved respectively. Then the phase A is added to the phase B, and the mixture is emulsified by an emulsifier. Then the emulsion is cooled by a heat exchanger and the cream is obtained.

Example 26 Cream

| A. Oily phase | |
|---|---|
| Cetanol | 4.0 |
| Vaseline | 7.0 |
| Isopropyl myristate | 8.0 |
| Squalane | 12.0 |
| Dimethyl polysiloxane | 3.0 |
| Monoglycerin stearate | 2.2 |
| POE (20) sorbitane monostearate | 0.5 |
| Stearyl glycyrrhetinate | 0.1 |
| BHT | 0.02 |
| Ethyl paraben | 0.1 |
| Butyl paraben | 0.1 |
| Propyl paraben | 0.1 |

| B. Aqueous phase | |
| --- | --- |
| 1,3 butylene glycol | 7.0 |
| Disodium edetate | 0.07 |
| Phenoxy ethanol | 0.2 |
| Magnesium L-ascorbyl-2-phosphate | 3.0 |
| Polyacrylic acid alkyl ester | 1.0 |
| Methyl p-glyceroxy cinnamate | 8.0 |
| Distilled water | Residual |

<Preparation process>

The cream was obtained according to the procedure as described in the Example 25.

Example 27 Milky Lotion

| A. Oily phase | |
| --- | --- |
| Oleil oleate | 3.0 |
| Vaseline | 7.0 |
| Squalane | 5.0 |
| Sorbitane-sesqui-oleate | 0.8 |
| Polyoxyethylene oleate (20 E.O.) | 1.2 |
| Glyceryl p-glyceroxy cinnamate | 3.0 |
| Methyl paraben | 0.1 |
| Perfume | 0.12 |
| B. Aqueous phase | |
| Dipropylenglycol | 5.0 |
| Ethanol | 3.0 |
| Carboxy vinyl polymer | 0.17 |
| Sodium hyaluronate | 0.01 |
| Alkyl polyacrylate | 1.0 |
| Glyceryl trimethoxy cinnamate | 4.0 |
| Potassium hydroxide | 0.08 |
| Sodium hexametaphosphate | 0.05 |
| Distilled water | Residual |

<Preparation process>

The milky lotion was obtained according to the same procedure as described in the Example 25.

Example 28 Cream

| A. Oily phase | |
| --- | --- |
| Behenyl alcohol | 0.5 |
| Cholesteryl 12-hydroxy stearate | 2.0 |
| Squalane | 7.0 |
| Jojoba oil | 5.0 |
| Self-emulsifying type glycerin monostearate | 2.5 |
| Polyoxyethylene sorbitane monostearate (20EO) | 1.5 |
| 2-hydroxy-4-methoxy benzophenone | 3.0 |
| Ethyl paraben | 0.2 |
| Butyl paraben | 0.1 |
| Propyl paraben | 0.1 |
| B. Aqueous phase | |
| Propylene glycol | 5.0 |
| Sodium edetate | 0.08 |
| Glycerin | 5.0 |
| Beegum (Montmorillonite) | 3.0 |
| Potassium hydroxide | 3.3 |
| Glyceryl p-methoxy cinnamate | 8.0 |
| Distilled water | Residual |

<Preparation process>

The cream was obtained according to the same procedure as described in the Example 25.

Example 29 Skin Lotion with powder

| A. Oily phase | |
| --- | --- |
| Ethanol | 8.0 |
| POE (60) glyceryl monoisostearate | 2.0 |
| L-menthol | 0.1 |
| Camphor | 0.1 |
| Methyl paraben | 0.2 |
| Perfume | q.s. |
| B. Aqueous phase | |
| Glycerin | 3.5 |
| Sodium glyceroxy cinnamate | 4.0 |
| Zinc oxide | 1.5 |
| Kaolin | 0.5 |
| Bentonite | 0.3 |
| Sodium hexamethaphosphate | 0.03 |
| Distilled water | Residual |

<Preparation process>

The skin lotion was obtained according to the same procedure as described in Example 25.

We claim:

1. An adduct of cinnamic acid and glycerin represented by the following structural formula (1):

$$(R-O-)_n \underset{(Ge-O-)_k}{\bigcirc} -CH=CH-\overset{O}{\underset{\|}{C}}OX \quad (1)$$

wherein in the structural formula (1) above, G represents 1 mole of glycerin and e represents average mole number of addition which is at least 1; and $(Ge-O-)_k$ is at the para position; R represents hydrogen or fatty chain; n and k are identified by $\{n+k\}$ is 1 to 3, and n and k are 0 to 3, respectively; X represents hydrogen, ion, fatty chain or Gm; G represents 1 mole of glycerin; and m represents average number of addition which is at least 1.

2. An ultraviolet absorbent comprising the adduct of cinnamic acid and glycerin according to claim 1.

3. An external preparation for skin comprising one or more types of the adduct of cinnamic acid and glycerin according to claim 1.

4. Applying to the skin a sunscreen comprising the composition of claim 1.

* * * * *